US009060927B2

(12) United States Patent
Steiner et al.

(10) Patent No.: US 9,060,927 B2
(45) Date of Patent: Jun. 23, 2015

(54) INSULIN FORMULATIONS FOR RAPID UPTAKE

(75) Inventors: Solomon S. Steiner, Mount Kisco, NY (US); Roderike Pohl, Sherman, CT (US); Ming Li, Yorktown Heights, NY (US); Robert Hauser, Columbia, MD (US)

(73) Assignee: Biodel Inc., Danbury, CT (US)

( * ) Notice: Subject to any disclaimer, the term of this patent is extended or adjusted under 35 U.S.C. 154(b) by 416 days.

(21) Appl. No.: 12/397,219

(22) Filed: Mar. 3, 2009

(65) Prior Publication Data
US 2010/0227795 A1   Sep. 9, 2010

(51) Int. Cl.
  A61K 38/28   (2006.01)
  C07K 14/62   (2006.01)
  A61K 9/00    (2006.01)
  A61K 38/00   (2006.01)

(52) U.S. Cl.
  CPC .............. A61K 9/0019 (2013.01); A61K 38/28 (2013.01); C07K 14/62 (2013.01); A61K 38/00 (2013.01)

(58) Field of Classification Search
  USPC .............. 530/303, 399; 514/5.9, 6.4, 6.5, 6.7, 514/6.8, 6.9
  See application file for complete search history.

(56) References Cited

U.S. PATENT DOCUMENTS

| | | |
|---|---|---|
| 2,143,590 A | 1/1939 | Scott |
| 2,626,228 A | 1/1953 | Petersen |
| 2,819,999 A | 1/1958 | Schlichtkrull |
| 3,649,456 A | 3/1972 | De Benneville et al. |
| 3,683,635 A | 8/1972 | Campanelli |
| 3,906,950 A | 9/1975 | Cocozza |
| 3,921,637 A | 11/1975 | Bennie et al. |
| 4,129,560 A | 12/1978 | Zoltobrocki |
| 4,153,689 A | 5/1979 | Hirai |
| 4,196,196 A | 4/1980 | Tiholiz |
| 4,211,769 A | 7/1980 | Okada |
| 4,272,398 A | 6/1981 | Jaffe |
| 4,294,829 A | 10/1981 | Suzuki |
| 4,343,898 A | 8/1982 | Markussen |
| 4,364,385 A | 12/1982 | Lossef |
| 4,377,482 A | 3/1983 | Rivier |
| 4,459,226 A | 7/1984 | Grimes |
| 4,489,159 A | 12/1984 | Markussen |
| 4,511,505 A | 4/1985 | Morihara |
| 4,659,696 A | 4/1987 | Hirai |
| 4,861,627 A | 8/1989 | Mathiowitz |
| 4,866,051 A | 9/1989 | Hunt |
| 4,925,673 A * | 5/1990 | Steiner et al. .................. 424/455 |
| 4,946,828 A | 8/1990 | Markussen |
| 5,006,343 A | 4/1991 | Benson |
| 5,042,975 A | 8/1991 | Chien |
| 5,145,684 A | 9/1992 | Liversidge et al. |
| 5,188,837 A | 2/1993 | Domb |
| 5,204,108 A | 4/1993 | Illum |
| 5,260,306 A | 11/1993 | Boardman et al. |
| 5,329,976 A | 7/1994 | Haber |
| 5,352,461 A | 10/1994 | Feldstein et al. |
| 5,354,562 A | 10/1994 | Platz |
| 5,364,838 A | 11/1994 | Rubsamen |
| 5,458,135 A | 10/1995 | Patton et al. |
| 5,474,978 A | 12/1995 | Bakaysa |
| 5,482,927 A | 1/1996 | Maniar |
| 5,484,606 A | 1/1996 | Dhabhar et al. |
| 5,492,112 A | 2/1996 | Mecikalski et al. |
| 5,503,852 A | 4/1996 | Steiner et al. |
| 5,514,646 A | 5/1996 | Chance et al. |
| 5,534,488 A | 7/1996 | Hoffmann |
| 5,547,929 A | 8/1996 | Anderson, Jr. et al. |
| 5,562,909 A | 10/1996 | Allcock et al. |
| 5,577,497 A | 11/1996 | Mecikalski et al. |
| 5,650,486 A | 7/1997 | Felippis |

(Continued)

FOREIGN PATENT DOCUMENTS

| | | |
|---|---|---|
| CA | 2 136 704 | 5/1995 |
| DE | 247684 | 7/1987 |

(Continued)

OTHER PUBLICATIONS

US 5,785,981, 7/1998, Stanley et al. (withdrawn).

(Continued)

*Primary Examiner* — Elizabeth C Kemmerer
*Assistant Examiner* — Regina M Deberry
(74) *Attorney, Agent, or Firm* — Pabst Patent Group LLP

(57) ABSTRACT

Injectable insulin formulations with improved stability and rapid onset of action are described herein. The formulations may be for subcutaneous, intradermal or intramuscular administration. In the preferred embodiment, the formulations are administered via subcutaneous injection. The formulations contain insulin in combination with a chelator and dissolution agent, and optionally additional excipients. In the preferred embodiment, the formulation contains human insulin, a zinc chelator such as EDTA and a dissolution agent such as citric acid or sodium citrate. These formulations are rapidly absorbed into the blood stream when administered by subcutaneous injection. In the preferred embodiment, the insulin is provided as a clear liquid, neutral pH, in a multi-use sterile vial. In an alternative embodiment, the insulin is provided as a powder in a sterile vial. This is mixed with a diluent containing a pharmaceutically acceptable carrier, such as water, a zinc chelator such as EDTA and a dissolution agent such as citric acid shortly before or at the time of administration. In another embodiment, the insulin is stored as a frozen mixture, ready for use upon thawing.

20 Claims, 13 Drawing Sheets

(56) References Cited

U.S. PATENT DOCUMENTS

| | | | |
|---|---|---|---|
| 5,653,961 A | 8/1997 | McNally et al. |
| 5,653,987 A | 8/1997 | Modi et al. |
| 5,658,878 A | 8/1997 | Bäckström et al. |
| 5,672,359 A | 9/1997 | Digenis |
| 5,693,338 A | 12/1997 | Milstein |
| 5,740,794 A | 4/1998 | Smith et al. |
| 5,747,445 A | 5/1998 | Bäckström et al. |
| 5,750,497 A | 5/1998 | Havelund |
| 5,763,396 A | 6/1998 | Weiner et al. |
| 5,766,620 A | 6/1998 | Ebert et al. |
| RE35,862 E | 7/1998 | Steiner et al. |
| 5,783,556 A * | 7/1998 | Clark et al. ............ 514/6.6 |
| 5,785,049 A | 7/1998 | Smith et al. |
| 5,785,989 A | 7/1998 | Stanley et al. |
| 5,807,315 A | 9/1998 | Van Antwerp et al. |
| 5,849,322 A | 12/1998 | Ebert et al. |
| 5,874,064 A | 2/1999 | Edwards et al. |
| 5,877,174 A | 3/1999 | Ono et al. |
| 5,888,477 A | 3/1999 | Gonda et al. |
| 5,898,028 A | 4/1999 | Jensen |
| 5,901,703 A | 5/1999 | Ohki et al. |
| 5,912,011 A | 6/1999 | Makino et al. |
| 5,929,027 A | 7/1999 | Takama et al. |
| 5,952,008 A | 9/1999 | Bäckström et al. |
| 5,976,569 A | 11/1999 | Milstein |
| 5,985,309 A | 11/1999 | Edwards et al. |
| 5,997,848 A | 12/1999 | Patton et al. |
| 6,051,256 A | 4/2000 | Platz et al. |
| 6,063,910 A | 5/2000 | Debenedetti |
| 6,071,497 A | 6/2000 | Steiner et al. |
| 6,099,517 A | 8/2000 | Daugherty |
| 6,132,766 A | 10/2000 | Sankaram et al. |
| 6,153,613 A | 11/2000 | Ono et al. |
| 6,165,484 A | 12/2000 | Raad |
| 6,180,141 B1 | 1/2001 | Lemercier |
| RE37,053 E | 2/2001 | Hanes et al. |
| 6,248,363 B1 | 6/2001 | Patel et al. |
| 6,254,854 B1 | 7/2001 | Edwards et al. |
| 6,264,981 B1 | 7/2001 | Zhang |
| 6,294,204 B1 | 9/2001 | Rossling et al. |
| 6,310,038 B1 | 10/2001 | Havelund |
| 6,331,318 B1 | 12/2001 | Milstein |
| 6,395,744 B1 | 5/2002 | Adams et al. |
| 6,395,774 B1 | 5/2002 | Milstein |
| 6,423,344 B1 | 7/2002 | Platz et al. |
| 6,428,771 B1 | 8/2002 | Steiner et al. |
| 6,432,383 B1 | 8/2002 | Modi |
| 6,436,443 B2 | 8/2002 | Edwards et al. |
| 6,440,463 B1 | 8/2002 | Feldstein et al. |
| 6,444,226 B1 | 9/2002 | Steiner et al. |
| 6,447,753 B2 | 9/2002 | Edwards et al. |
| 6,465,425 B1 | 10/2002 | Tracy |
| 6,503,480 B1 | 1/2003 | Edwards et al. |
| 6,518,239 B1 | 2/2003 | Kuo et al. |
| 6,582,728 B1 | 6/2003 | Platz |
| 6,592,904 B2 | 7/2003 | Platz et al. |
| 6,635,283 B2 | 10/2003 | Edwards et al. |
| 6,652,885 B2 | 11/2003 | Steiner et al. |
| 6,676,931 B2 | 1/2004 | Dugger |
| 6,685,967 B1 | 2/2004 | Patton |
| 6,737,045 B2 | 5/2004 | Patton |
| 6,949,258 B2 | 9/2005 | Zhang |
| 6,960,561 B2 | 11/2005 | Boderke |
| 7,030,084 B2 | 4/2006 | Ekwuribe et al. |
| 7,089,934 B2 | 8/2006 | Staniforth et al. |
| 7,192,919 B2 | 3/2007 | Tzannis |
| 7,279,457 B2 * | 10/2007 | Pohl et al. ............ 514/5.9 |
| 7,713,929 B2 * | 5/2010 | Steiner et al. ............ 514/5.9 |
| 7,718,609 B2 * | 5/2010 | Steiner et al. ............ 514/5.9 |
| 2001/0039260 A1 | 11/2001 | Havelund |
| 2001/0043934 A1 | 11/2001 | L'Italien et al. |
| 2002/0028767 A1 | 3/2002 | Jensen |
| 2002/0198140 A1 | 12/2002 | Havelund |
| 2003/0017211 A1 | 1/2003 | Steiner |
| 2003/0064097 A1 | 4/2003 | Patel et al. |
| 2003/0068378 A1 | 4/2003 | Chen et al. |
| 2003/0143195 A1 | 7/2003 | Pinsker |
| 2003/0172924 A1 | 9/2003 | Staniforth et al. |
| 2003/0194420 A1 | 10/2003 | Holl et al. |
| 2004/0048783 A1 | 3/2004 | Brunner-Schwarz |
| 2004/0077528 A1 | 4/2004 | Steiner |
| 2004/0096403 A1 | 5/2004 | Steiner |
| 2004/0151774 A1 | 8/2004 | Pauletti et al. |
| 2004/0157928 A1 | 8/2004 | Kim et al. |
| 2004/0182387 A1 | 9/2004 | Steiner |
| 2004/0247628 A1 | 12/2004 | Lintz et al. |
| 2005/0080000 A1 | 4/2005 | Thurow et al. |
| 2005/0153874 A1 | 7/2005 | Cheatham |
| 2005/0203001 A1 | 9/2005 | Arbit |
| 2005/0214251 A1 | 9/2005 | Pohl et al. |
| 2006/0067891 A1 | 3/2006 | Modi |
| 2007/0086952 A1 | 4/2007 | Steiner |
| 2007/0134279 A1 | 6/2007 | Stern |
| 2007/0155654 A1 | 7/2007 | Langkjaer |
| 2007/0235365 A1 | 10/2007 | Pohl et al. |
| 2008/0039368 A1 | 2/2008 | Steiner et al. |
| 2008/0085298 A1 | 4/2008 | Pohl et al. |
| 2008/0090753 A1 | 4/2008 | Pohl et al. |
| 2008/0096800 A1 | 4/2008 | Pohl et al. |
| 2008/0175923 A1 | 7/2008 | Martin |
| 2009/0137455 A1 | 5/2009 | Steiner et al. |
| 2009/0175840 A1 | 7/2009 | Kashyap et al. |
| 2009/0215669 A1 * | 8/2009 | Myers et al. ............ 514/4 |
| 2009/0304665 A1 * | 12/2009 | Frost et al. ............ 424/94.5 |
| 2009/0325860 A1 | 12/2009 | Costantino |
| 2013/0053315 A1 * | 2/2013 | Lau et al. ............ 514/11.7 |

FOREIGN PATENT DOCUMENTS

| | | |
|---|---|---|
| EM | 1 114 644 | 7/2001 |
| EP | 0 069 715 | 1/1983 |
| EP | 0 122 036 | 10/1984 |
| EP | 0 220 958 A2 | 5/1987 |
| EP | 0 237 507 | 9/1987 |
| EP | 0 257 915 | 2/1988 |
| EP | 0 360 340 | 3/1990 |
| EP | 0 364 235 | 4/1990 |
| EP | 0 606 486 | 12/1993 |
| EP | 0748213 | 12/1996 |
| EP | 1 428 524 | 6/2004 |
| GB | 2 069 502 | 8/1981 |
| GB | 2240337 | 7/1991 |
| JP | 2149545 | 2/1992 |
| JP | 63020301 A | 1/1998 |
| WO | 8300288 | 2/1983 |
| WO | WO 90/13285 | 11/1990 |
| WO | WO 91/04011 | 4/1991 |
| WO | WO 91/08764 | 6/1991 |
| WO | WO 91/16882 | 11/1991 |
| WO | WO 92/04069 | 3/1992 |
| WO | WO 92/08509 | 5/1992 |
| WO | WO 93/02712 | 2/1993 |
| WO | WO 93/17728 | 9/1993 |
| WO | WO 93/18754 | 9/1993 |
| WO | WO 94/00291 | 1/1994 |
| WO | WO 95/00127 | 5/1995 |
| WO | WO 95/11666 | 5/1995 |
| WO | 9524183 | 9/1995 |
| WO | WO 95/31979 | 11/1995 |
| WO | WO 95/34294 | 12/1995 |
| WO | WO 96/10996 | 4/1996 |
| WO | WO 96/36314 A2 | 11/1996 |
| WO | WO 96/36352 | 11/1996 |
| WO | WO 97/33531 | 9/1997 |
| WO | WO 97/49386 | 12/1997 |
| WO | WO 98/42367 | 10/1998 |
| WO | WO 98/42368 | 10/1998 |
| WO | WO 98/42749 | 10/1998 |
| WO | WO 99/52506 A1 | 10/1999 |
| WO | 9934821 | 10/2000 |
| WO | WO 01/00654 | 1/2001 |
| WO | WO 01/07107 | 2/2001 |
| WO | WO 02/11676 | 2/2002 |
| WO | WO 03/057170 | 7/2003 |

(56) References Cited

FOREIGN PATENT DOCUMENTS

| WO | WO 03/086345 | 10/2003 |
|---|---|---|
| WO | WO 03/094951 | 11/2003 |
| WO | WO 03/101395 | 12/2003 |
| WO | WO 2004/056314 | 7/2004 |
| WO | WO 2004/075919 | 9/2004 |
| WO | WO 2004/080401 | 9/2004 |
| WO | WO 2005/089722 | 9/2005 |
| WO | WO 2006/088473 | 8/2006 |
| WO | WO 2007/041481 | 4/2007 |
| WO | WO 2007/047948 | 4/2007 |
| WO | WO 2007/121256 | 10/2007 |
| WO | 2008084237 | 7/2008 |
| WO | WO 2008/084237 | 7/2008 |
| WO | 2009134380 | 11/2009 |

OTHER PUBLICATIONS

Berge, et al. "Pharmacuetical Salts," *J. Pharmaceutical Sciences* 66(1):1-19 (1977).
Brange, et al., "Chemical stability of insulin1: hydrolytic degradation during storage of pharmaceutical preparations", *Pharm. Res.*, 9:715-726 (1992).
Brange and Langkjoer, "Insulin structure and stability", *Pharm Biotechnol.*, 5:315-350 (1993).
Cerasi, et al., "Decreased sensitivity of the pancreatic beta cells to glucose in prediabetic and diabetic subjects. A glucose dose-response study," *Diabetes* 21(4): 224-34 (1972).
Cheatham and Pfeutzner, "Desirable dynamics & performance of inhaled insulin compared to subcutaneous insulin given at mealtime in type 2 diabetes: A report from the technosphereinsulin study group" *Diabetes Technology & Therapeutics* 6:234-235 (2004).
Culy, et al., "Management of diabetes mellitus: Defining the role of insulin lispro mix 75/25", *Dis. Man. Health. Outcome*, 9(12):711-730 (2001).
Davidson, et al.,"Effect of premixed nph and regular insulin on glucose control and health-related quality of life in patients with type 2 diabetes mellitus", *Endocrine Practice*, 3(6):331-336(1997).
De Sousa, et al., "Biocompatibility of EDTA, EGTA and citric acid", *Braz. Dent. J.*, 16:3-8 (2005).
Dunn, "Zinc-ligand interactions modulate assembly and stability of the insulin hexamer", *Biometals*, 18(4):295-303 (2005).
Edelman, "Type II Diabetes Mellitus," *Advances in Internal Medicine*, 43:449-500 (1998).(Abstract).
Edelman, et al., "A double-blinded placebo-controlled trial assessing pramlintide treatment in the setting of intensive insulin therapy in type 1 diabetes", *Diabetes Care*, 29(10):2189-2195 (2006).
Engelgau, et al., "Screening for tyoe 2 diabetes," *Diabetes Care* 1563(23):1-31 (2000).
Garber, "Premixed insulin analogues for the treatment of diabetes mellitus", *Drugs*, 66(1):31-49 (2006).
Hagedorn, et al., "Protamine insulin", *JAMA*, 106:177-180 (1936).
Hanley et al., "Cross-sectional and prospective associations between proinsulin and cardiovascular disease risk factors in a population experiencing rapid cultural transition" *Diabetes Care* 24(7):1240-1247 (2001).
Huebner, et al. "Uber inhalation von insulin", *Klinische Wochenschrift* 16:2342-3 (1924) (with English Abstract).
Kang, et al., "Subcutaneous insulin absorption explained by insulin's physiochemical properties", *Diabetes Care*, 14:942-948 (1991).
Klauser, et al., "Mixtures of human intermediate and human regular insulin in type 1 diabetic patients", *Diabetes Res. And Clin. Practice*, 5:185-190 (1988).
Lalli, et al., "Long-term intensive treatment of type 1 diabetes with the short-acting insulin analog lispro in variable combination with NPH insulin at mealtime", *Diabetes Care*, 22(3):468-477 (1999).
Leahy, "Beta-cell dysfunction in type II diabetes mellitus," *Curr. Opin. Endocrinol. Diabetes* 2(4): 300-306 (1995).
Molitch, et al., "How long should insulin be used once a vial is started?", *Diabetes Care*, 27(5):1240-1241; author reply 1241-1242 (2004).

Monch & Dehnen, "High-performance liquid chromatography of polypeptides and proteins on a reversed-phase support", *Journal of Chromatography*,147:415-418 (1978).
Pfeiffer, "Insulin secretion in diabetes mellitus," *Am. J. Med.* 70(3): 579.88 (1981).
Pfutzner, et al., "Influence of small dose i.v., s.c. and pulmonary insulin treatment on prandial glucose control in patients with type 2 diabetes" 37$^{th}$ *Annual Meeting of the EASD*, Glasgow, Sep. 9-13, 2001 812 (2001) (abstract).
Plum, et al., "Pharmacokinetics of the rapid-acting insulin analog, insulin aspart, in rats, dogs, and pigs, and pharmacodynamics of insulin aspart in pigs.", *Drug Metab. Dispos.*, 28(2):155-60 (2000).
Polonsky, et al., "Abnormal patterns of insulin secretion in non-insulin-dependent diabetes mellitus," *N. England J. Med.* 318(19):1231.39 (1988).
Prabhu, et al. "A study of factors controlling dissolution kinetic of zinc complexed protein suspensions in various ionic species", *Int. J. Pharm.*, 217(1-2):71.8 (2001).
Quinn, et al., "Minimizing the aggregation of insulin solutions", *J. Pharmaceutical Sci.*, 72:1472.1473 (1983).
Raskin, et al., "Continuous subcutaneous insulin infusion and multiple daily injection therapy are equally effective in type 2 diabetes" *Diabetes Care* 26:2598-2603 (2003).
Raz, et al. "Pharmacodynamic and pharmacokinetics of dose ranging effects of oralin versus s.c. regular insulin in Type 1 diabetic patients," *Fourth Annual Diabetes Technology Meeting*, Philadelphia, PA, 2004, Abstract.
Roach, et al., "Improved postprandial glycemic control during treatment with Humalog Mix25, a novel protamine-based insulin lispro formulation. Humalog Mix25 Study Group", *Diabetes Care*, 22(8):1258-1261 (1999).
Schneider, et al., "Stimulation by proinsulin of expression of plasminogen activator inhibitor type-I in endothelial cells" *Diabetes* 41(7):890-895 (1992).
Warren, et al., "Postprandial versus preprandial dosing of biphasic insulin aspart in elderly type 2 diabetes patients" *Diabetes Research and Clinical Practive* 66:23-29 (2004).
Wigley, et al., "Insulin across respiratory mucosae by aerosol delivery," *Diabetes* 20(8): 552-556 (1971).
Steiner, et al., "A novel insulin formulation with a more rapid onset of action", *Diabetologia*, 51(9):1602-1606 (2008).
Actrapid Summary of Product Characteristics, retrieved from http://emc.medicines.org.uk/medicine/3513/SPC/Actrapid+100+IU+ml,+Solution+for+Injection+in+a+vial/, pp. 1-6. [Retrieved on Apr. 20, 2009].
Bell, et al., "Human Insulin", GenBank Accession No. AAA59172, pp. 1-2, retrieved from http://www.ncbi.nlm.nih.gov/entrez/viewer.fcgi?db=protein&id=386828 [retrieved on Feb. 17, 2009].
Flisikowski, et al. "Bovine Insulin", Genbank Accession No. ACD35246 retrieved from http://www.ncbi.nlm.nih.gov/gene?term=acd35246 [retrieved on Feb. 17, 2009].
Humalog, Mix 75/25TM "Patient Information", Eli Lilly, pp. 1-4, retrieved from http://pi.lilly.com/us/humalog7525-pi.pdf [retrieved on Jun. 18, 2009].
"FDA Approves Rapid-Acting Insulin Apidra® for Treatment of Children with Diabetes", retrieved from http://www.medicalnewstoday.com/releases/127409.php [retrieved on Apr. 28, 2009].
"Insulin" Diabetes Forecast, 2008 Resource Guide, RGI 1-RG14. (2008).
Becker, "Insulin glulisine complementing basal insulins: A review of structure and activity", Diabetes Tech and Therp., 9(1):109-21 (2007).
Gaetani, et al., "Catalase and glutathione peroxidase are equally active in detoxification of hydrogen peroxide in human erythrocytes", Blood Journal, 73 (1):334-339 (1989).
Gerich, "Insulin glargine: long-acting basal insulin analog for improved metabolic control", Curr. Med. Res. & Opin., 20(1):31-37 (2004).

(56) References Cited

OTHER PUBLICATIONS

Kashyap, et al., "Design and evaluation of biodegradable, biosensitive in situ gelling system for pulsatile delivery of insulin", Biomaterials, 27:2051-60 (2007).

Rungby, et al., "New strategies in insulin treatment: analogues and noninvasive routes of administration", Fundamental & Clinical Pharm., 19:127-32 (2004).

Traitel, et al., "Characterization of glucose-sensitive insulin release systems in simulated in vivo conditions", Biomaterials, 21:1679-87 (2000).

IUBMB Eniyme Nomenclature, EC 1.11.1.6, 1 page, accessed Feb. 6, 2012 from www.chem.qmul.ac.uk/iubmb/enzyme/EC1/11/1/6.html, originated 1961, updated 1999.

Wermuth, Glossary of Terms used in medicinal chemistry, Pure Appl. Chem., 70(5):1129-43 (1998).

Buse, "Insulin glargine (HOE901). First responsibilities: understanding the data and ensuring safety", Diabetes Care, 23(5):576-8 (2000).

Poulsen, et al., "Precipitation of insulin products used for continuous subcutaneous insulin infusion", Diabetes Tech Therap., 7(1):142-50 (2005).

\* cited by examiner

INSULIN FORMULATIONS FOR RAPID UPTAKE

FIELD OF THE INVENTION

The invention is in the general field of injectable rapid acting drug delivery insulin formulations.

BACKGROUND OF THE INVENTION

Diabetes Overview

Glucose is a simple sugar used by all the cells of the body to produce energy and support life. Humans need a minimum level of glucose in their blood at all times to stay alive. The primary manner in which the body produces blood glucose is through the digestion of food. When a person is not getting this glucose from food digestion, glucose is produced from stores in the tissue and released by the liver. The body's glucose levels are regulated by insulin. Insulin is a peptide hormone that is naturally secreted by the pancreas. Insulin helps glucose enter the body's cells to provide a vital source of energy.

When a healthy individual begins a meal, the pancreas releases a natural spike of insulin called the first-phase insulin release. In addition to providing sufficient insulin to process the glucose coming into the blood from digestion of the meal, the first-phase insulin release acts as a signal to the liver to stop making glucose while digestion of the meal is taking place. Because the liver is not producing glucose and there is sufficient additional insulin to process the glucose from digestion, the blood glucose levels of healthy individuals remain relatively constant and their blood glucose levels do not become too high.

Diabetes is a disease characterized by abnormally high levels of blood glucose and inadequate levels of insulin. There are two major types of diabetes—Type 1 and Type 2. In Type 1 diabetes, the body produces no insulin. In the early stages of Type 2 diabetes, although the pancreas does produce insulin, either the body does not produce the insulin at the right time or the body's cells ignore the insulin, a condition known as insulin resistance.

Even before any other symptoms are present, one of the first effects of Type 2 diabetes is the loss of the meal-induced first-phase insulin release. In the absence of the first-phase insulin release, the liver will not receive its signal to stop making glucose. As a result, the liver will continue to produce glucose at a time when the body begins to produce new glucose through the digestion of the meal. As a result, the blood glucose level of patients with diabetes goes too high after eating, a condition known as hyperglycemia. Hyperglycemia causes glucose to attach unnaturally to certain proteins in the blood, interfering with the proteins' ability to perform their normal function of maintaining the integrity of the small blood vessels. With hyperglycemia occurring after each meal, the tiny blood vessels eventually break down and leak. The long-term adverse effects of hyperglycemia include blindness, loss of kidney function, nerve damage and loss of sensation and poor circulation in the periphery, potentially requiring amputation of the extremities.

Between two and three hours after a meal, an untreated diabetic's blood glucose becomes so elevated that the pancreas receives a signal to secrete an inordinately large amount of insulin. In a patient with early Type 2 diabetes, the pancreas can still respond and secretes this large amount of insulin. However, this occurs at the time when digestion is almost over and blood glucose levels should begin to fall. This inordinately large amount of insulin has two detrimental effects. First, it puts an undue extreme demand on an already compromised pancreas, which may lead to its more rapid deterioration and eventually render the pancreas unable to produce insulin. Second, too much insulin after digestion leads to weight gain, which may further exacerbate the disease condition.

Current Treatments for Diabetes and their Limitations

Because patients with Type 1 diabetes produce no insulin, the primary treatment for Type 1 diabetes is daily intensive insulin therapy. The treatment of Type 2 diabetes typically starts with management of diet and exercise. Although helpful in the short-run, treatment through diet and exercise alone is not an effective long-term solution for the vast majority of patients with Type 2 diabetes. When diet and exercise are no longer sufficient, treatment commences with various non-insulin oral medications. These oral medications act by increasing the amount of insulin produced by the pancreas, by increasing the sensitivity of insulin-sensitive cells, by reducing the glucose output of the liver or by some combination of these mechanisms. These treatments are limited in their ability to manage the disease effectively and generally have significant side effects, such as weight gain and hypertension. Because of the limitations of non-insulin treatments, many patients with Type 2 diabetes deteriorate over time and eventually require insulin therapy to support their metabolism.

Insulin therapy has been used for more than 80 years to treat diabetes. This therapy usually involves administering several injections of insulin each day. These injections consist of administering a long-acting basal injection one or two times per day and an injection of a fast acting insulin at meal-time. Although this treatment regimen is accepted as effective, it has limitations. First, patients generally dislike injecting themselves with insulin due to the inconvenience and pain of needles. As a result, patients tend not to comply adequately with the prescribed treatment regimens and are often improperly medicated.

More importantly, even when properly administered, insulin injections do not replicate the natural time-action profile of insulin. In particular, the natural spike of the first-phase insulin release in a person without diabetes results in blood insulin levels rising within several minutes of the entry into the blood of glucose from a meal. By contrast, injected insulin enters the blood slowly, with peak insulin levels occurring within 80 to 100 minutes following the injection of regular human insulin.

A potential solution is the injection of insulin directly into the vein of diabetic patients immediately before eating a meal. In studies of intravenous injections of insulin, patients exhibited better control of their blood glucose for 3 to 6 hours following the meal. However, for a variety of medical reasons, intravenous injection of insulin before each meal is not a practical therapy.

One of the key improvements in insulin treatments was the introduction in the 1990s of rapid-acting insulin analogs, such as insulin lispro (IL), insulin aspart (IA) and insulin glulisine (IG). However, even with the rapid-acting insulin analogs, peak insulin levels typically occur within 50 to 90 minutes following the injection. Because the rapid-acting insulin analogs do not adequately mimic the first-phase insulin release, diabetics using insulin therapy continue to have inadequate levels of insulin present at the initiation of a meal and too much insulin present between meals. This lag in insulin delivery can result in hyperglycemia early after meal onset. Furthermore, the excessive insulin between meals may result in an abnormally low level of blood glucose known as hypoglycemia. Hypoglycemia can result in loss of mental acuity, confusion, increased heart rate, hunger, sweating and faintness. At very low glucose levels, hypoglycemia can result in loss of consciousness, coma and even death. According to the American Diabetes Association, or ADA, insulin-using diabetic patients have on average 1.2 serious hypoglycemic events per year, many of which events require hospital emergency room visits by the patients.

Because the time-course of insulin delivery to the blood plays such an important role in overall glucose control, there is significant need for insulin an injectable insulin that reaches the blood more rapidly than the rapid acting insulin analogs.

Therefore, it is an object of the invention to provide rapid acting injectable insulin compositions with improved stability and rapid onset of action.

SUMMARY OF THE INVENTION

Injectable insulin formulations with improved stability and rapid onset of action are described herein. The formulations may be for subcutaneous, intradermal or intramuscular administration. In the preferred embodiment, the formulations are administered via subcutaneous injection. The formulations contain insulin in combination with a chelator and dissolution agent, and optionally additional excipients. In the preferred embodiment, the formulation contains human insulin, a zinc chelator such as EDTA and a dissolution agent such as citric acid or a salt thereof such as sodium citrate. These formulations are rapidly absorbed into the blood stream when administered by subcutaneous injection. Examples demonstrate that one can increase pH to physiological pH and still obtain dissolution and rapid uptake of the insulin.

In one embodiment, the insulin is provided as a dry powder in a sterile vial. This is mixed with a diluent containing a pharmaceutically acceptable carrier, such as water, and optionally a zinc chelator such as EDTA and/or a dissolution agent such as citric acid shortly before or at the time of administration. In another embodiment, the insulin, usually at a pH of approximately 4, is stored as a frozen mixture, ready for use upon thawing. In the preferred embodiment, the insulin is provided as an aqueous solution at pH 7, which is stored at 4° C.

BRIEF DESCRIPTION OF THE DRAWINGS

FIG. 3a, Aspartic acid (0.47 mg/mL), Glutamic acid (0.74 mg/mL), Succinic acid (0.41 mg/mL), Adipic acid (0.73 mg/mL) and Citric acid (0.29 mg/mL and 0.56 mg/mL), pH range 3.2-3.8. FIG. 3b, Maleic (0.32 mg/ml), Fumaric acid (1.28 mg/mL) and Oxalic acid (0.32 mg/mL), pH range 2-3. Two time periods (10 and 30 min.) were selected for comparative analysis. Results are mean plus or minus standard error measured, n=4.

FIG. 5 is a graph of the transport of insulin (1 mg/mL) from a solution containing glutamic acid, citric acid or HCl to which different chelators at the same molar concentration ($4.84 \times 10^{-3}$ Mol) were added through oral epithelial cells was measured (cumulative insulin, micromoles). The chelators were no chelator (control), EDTA, EGTA, DMSA, CDTA, and TSC.

DETAILED DESCRIPTION OF THE INVENTION

Figure 1:
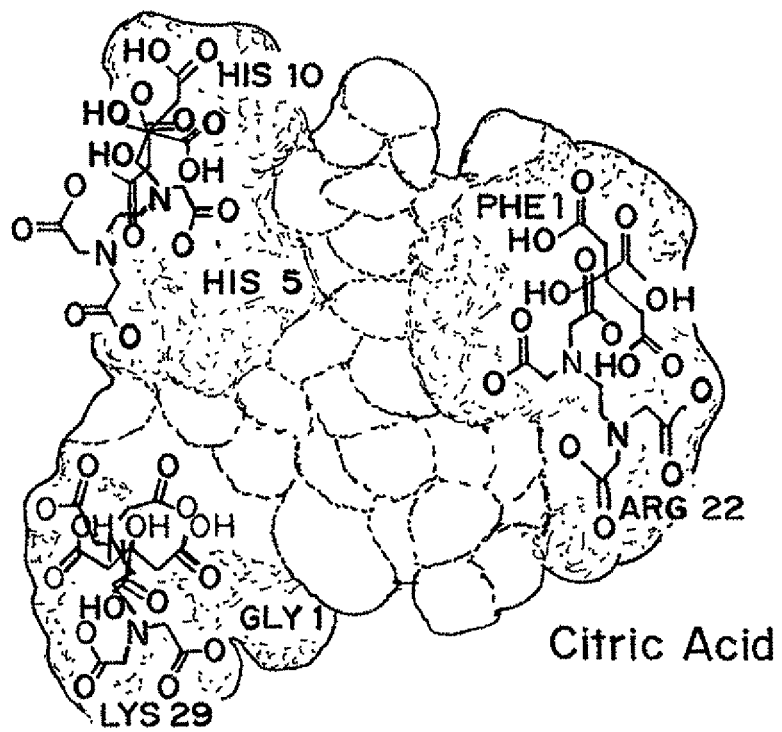
FIG. 1 is a three dimensional schematic of insulin showing exposed surface charges and overlaid with molecules ("dissolution and chelating agents") of appropriate size to mask the charge.

The insulin formulations of injectable human insulin described herein are administered immediately prior to a meal or at the end of a meal. In the preferred embodiment, the formulation combines recombinant human insulin with specific ingredients generally regarded as safe by the FDA. The formulation is designed to be absorbed into the blood faster than the currently marketed rapid-acting insulin analogs. One of the key features of the formulation of insulin is that it allows the insulin to disassociate, or separate, from the six molecule, or hexameric, form of insulin to the monomeric or dimeric form of insulin and deters re-association to the hexameric form. It is believed that by favoring the monomeric or dimeric form, this formulation allows for more rapid delivery of insulin into the blood as the human body requires insulin to be in the form of a single molecule before it can be absorbed into the body to produce its desired biological effects. Most human insulin that is sold for injection is in the hexameric form. This makes it more difficult for the body to absorb, as the insulin hexamer must first disassociate to form dimers and then monomers.

I. DEFINITIONS

As used herein, "insuin" refers to human or non-human, recombinant, purified or synthetic insulin or insulin analogues, unless otherwise specified:

As used herein, "Human insulin" is the human peptide hormone secreted by the pancreas, whether isolated from a natural source or made by genetically altered microorganisms. As used herein, "non-human insulin" is the same as human insulin but from an animal source such as pig or cow.

As used herein, an insulin analogue is an altered insulin, different from the insulin secreted by the pancreas, but still available to the body for performing the same action as natural insulin. Through genetic engineering of the underlying DNA, the amino acid sequence of insulin can be changed to alter its ADME (absorption, distribution, metabolism, and excretion) characteristics. Examples include insulin lispro, insulin glargine, insulin aspart, insulin glulisine, insulin detemir. The insulin can also be modified chemically, for example, by acetylation. As used herein, human insulin analogues are altered human insulin which is able to perform the same biological action as human insulin.

As used herein, a "chelator" or "chelating agent", refers to a chemical compound that has the ability to form one or more bonds to zinc ions. The bonds are typically ionic or coordination bonds. The chelator can be an inorganic or an organic compound. A chelate complex is a complex in which the metal ion is bound to two or more atoms of the chelating agent.

As used herein, a "solubilizing agent", is a compound that increases the solubility of materials in a solvent, for example, insulin in an aqueous solution. Examples of solubilizing agents include surfactants (TWEENS®); solvent, such as ethanol; micelle forming compounds, such as oxyethylene monostearate; and pH-modifying agents.

As used herein, a "dissolution agent" is an acid or salt that, when added to insulin and EDTA, enhances the transport and absorption of insulin relative to HCl and EDTA at the same pH, as measured using the epithelial cell transwell plate assay described in the examples below. HCl is not a dissolution agent but may be a solubilizing agent. Citric acid and sodium citrate are dissolution agents when measured in this assay. It is believed this is achieved at least in part by masking charges on the insulin, some of which are exposed during dissociation from the hexamer.

As used herein, an "excipient" is an inactive substance other than a chelator or dissolution agent, used as a carrier for the insulin or used to aid the process by which a product is manufactured. In such cases, the active substance is dissolved or mixed with an excipient.

As used herein, a "physiological pH" is between 6.8 and 7.6, preferably between 7 and 7.5, most preferably about 7.4.

As used herein, VIAJECT™ is the trademark for a recombinant human insulin formulated with a dissolution agent such as citric acid and a chelator such as EDTA. Viaject 25 U/mL (CE 25-4) contains 25 U/mL regular recombinant human insulin, 1.8 mg/mL Citric acid, 1.8 mg/mL disodium EDTA, 0.82% NaCl (isotonicity) and 3 mg/mL m-cresol. It is provided as an aqueous solution which is stored frozen, or in a two part kit consisting of dry powder insulin and diluent, at least one of which contains citric acid and EDTA. The pH of both reconstituted mixture and frozen solution is approximately pH 4. Viaject 100 U/mL (CE 100-4) contains 100 U/mL regular recombinant human insulin, 1.8 mg/mL citric acid, 1.8 mg/mL disodium EDTA, 22 mg/mL glycerin, 3 mg/mL m-cresol. This is also provided either as a frozen aqueous solution or two part kit consisting of dry powdered insulin and diluent. The pH of both of the reconstituted mixture and frozen solution is approximately 4, Viaject 100 U/mL (CE 100-7) contains 100 U/mL regular recombinant human insulin, 1.8 mg/mL citric acid, 1.8 mg/mL disodium EDTA, 22 mg/mL glycerin, 3 mg/mL m-cresol. This is provided as an aqueous solution having a pH of about 7.4, which can be stored at 4° C. VIAject with acid salts (CSE 100-7) is made by adding 1.8 mg/mL of both EDTA and trisodium citrate to water, then adding 100 U/mL insulin, reducing pH to 6, then raising pH to 7.4.

Formulations

Formulations include insulin, a chelator and a dissolution agent(s) and, optionally, one or more other excipients. In the preferred embodiment, the formulations are suitable for subcutaneous administration and are rapidly absorbed into the fatty subcutaneous tissue. The choice of dissolution agent and chelator, the concentration of both the dissolution agent and the chelator, and the pH that the formulation is adjusted to, all have a profound effect on the efficacy of the system. While many combinations have efficacy, the preferred embodiment is chosen for many reasons, including safety, stability, regulatory profile, and performance.

In the preferred embodiment, at least one of the formulation ingredients is selected to mask charges on the active agent. This may facilitate the transmembrane transport of the insulin and thereby increase both the onset of action and bioavailability for the insulin. The ingredients are also selected to form compositions that dissolve rapidly in aqueous medium. Preferably the insulin is absorbed and transported to the plasma quickly, resulting in a rapid onset of action (preferably beginning within about 5 minutes following administration and peaking at about 15-30 minutes following administration).

The chelator, such as EDTA, chelates the zinc in the insulin, removing the zinc from the insulin solution. This causes the insulin to take on its dimeric and monomeric form and retards reassembly into the hexamer state. Studies described in the examples indicate that the overall size of the dissociating hexamer is larger than the zinc complexed insulin hexamer, which then forms smaller units. Since the hexamers, dimers and monomers exist in a concentration-driven equilibrium, as the monomers are absorbed, more monomers are created. Thus, as insulin monomers are absorbed through the subcutaneous tissue, additional dimers dissemble to form more monomers. The completely dissociated monomeric form has a molecular weight that is less than one-sixth the molecular weight of the hexameric form, thereby markedly increasing both the speed and quantity of insulin absorption. To the extent that the chelator (such as EDTA) and/or dissolution agent (such as citric acid) hydrogen bond with the insulin, it is believed that it masks the charge on the insulin, facilitating its transmembrane transport and thereby increasing both the onset of action and bioavailability for insulin.

Insulin

The insulin can be recombinant or purified from a natural source. The insulin can be human or non-human. Human is preferred. In the most preferred embodiment, the insulin is human recombinant insulin. Recombinant human insulin is available from a number of sources. The insulin may also be an insulin analogue which may be based on the amino acid sequence of human insulin but having one or more amino acids differences, or a chemically modified insulin or insulin analog.

The dosages of the insulin depend on its bioavailability and the patient to be treated. Insulin is generally included in a dosage range of 1.5-100 IU, preferably 3-50 IU per human dose. Typically, insulin is provided in 100 IU vials.

Dissolution Agents

Figure 2:
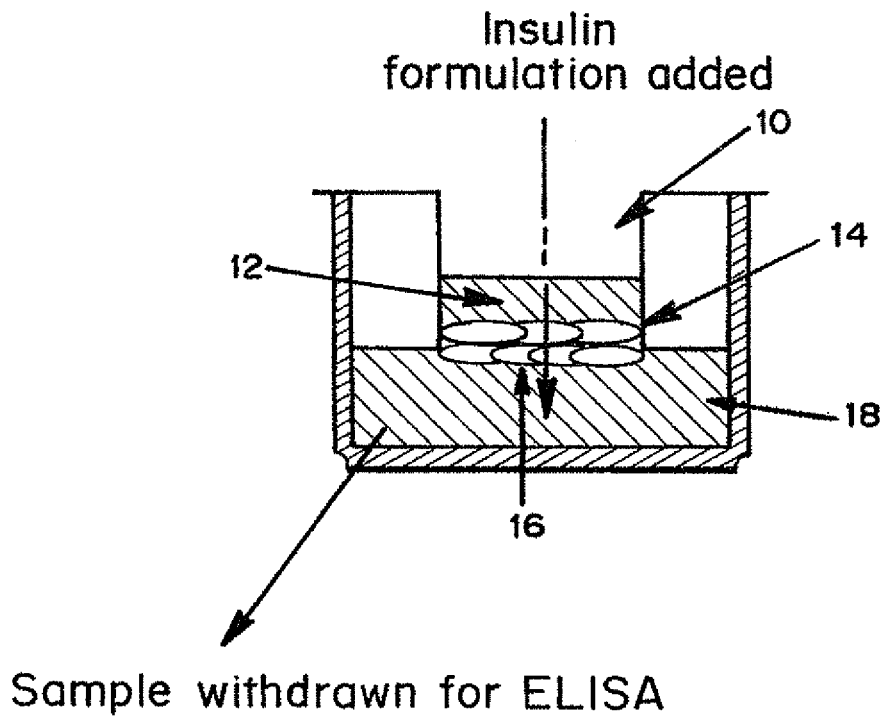
FIG. 2 is a schematic diagram of the transwell device 10 used to measure insulin absorption from a donor chamber 12 through 4-5 layers of immortalized oral epithelial cells 14 on a 0.1 micron filter 16 into a receiver chamber 18.

Certain acids, or their salts, appear to mask charges on the insulin, enhancing uptake and transport, as shown in FIG. 2. Those acids which are effective as dissolution agents include acetic acid, ascorbic acid, citric acid, glutamic, aspartic, succinic, fumaric, maleic, and adipic, relative to hydrochloric acid, as measured in the transwell assay described in the examples below. For example, if the active agent is insulin, a preferred dissolution agent is citric acid. Hydrochloric acid and sodium hydroxide are preferred agents for pH adjustment. HCl may be used in combination with any of the formulations, but is not a dissolution agent. Salts of the acids include sodium acetate, ascorbate, citrate, glutamate, aspartate, succinate, fumarate, maleate, and adipate. Salts of organic acids can be prepared using a variety of bases including, but not limited to, metal hydroxides, metal oxides, metal carbonates and bicarbonates, metal amines, as well as ammonium bases, such as ammonium chloride, ammonium carbonate, etc. Suitable metals include monovalent and polyvalent metal ions. Exemplary metals ions include the Group I metals, such as lithium, sodium, and potassium; Group II metals, such as barium, magnesium, calcium, and strontium; and metalloids such as aluminum. Polyvalent metal ions may be desirable for organic acids containing more than carboxylic acid group since these ions can simultaneously complex to more than one carboxylic acid group.

The range of dissolution agent corresponds to an effective amount of citric acid in combination with insulin and EDTA of between $9.37 \times 10^{-4}$ M to $9.37 \times 10^{-2}$ M citric acid.

Chelators

In the preferred embodiment, a zinc chelator is mixed with the insulin. The chelator may be ionic or non-ionic. Suitable chelators include ethylenediaminetetraacetic acid (EDTA), EGTA, alginic acid, alpha lipoic acid, dimercaptosuccinic acid (DMSA), CDTA (1,2-diaminocyclohexanetetraacetic acid), trisodium citrate (TSC). Hydrochloric acid is used in conjunction with TSC to adjust the pH, and in the process gives rise to the formation of citric acid, which is a dissolution agent.

In the preferred embodiment, the chelator is EDTA. The chelator captures the zinc from the insulin, thereby favoring the dimeric form of the insulin over the hexameric form and facilitating absorption of the insulin by the tissues surrounding the site of administration (e.g. mucosa, or fatty tissue). In addition, the chelator hydrogen may bond to the active agent, thereby aiding the charge masking of the insulin monomers and facilitating transmembrane transport of the insulin monomers.

The range of chelator corresponds to an effective amount of EDTA in combination with insulin and citric acid of between $2.42 \times 10^{-4}$ M to $9.68 \times 10^{-2}$ M EDTA.

Excipients

Pharmaceutical compositions may be formulated in a conventional manner using one or more physiologically acceptable carriers comprising excipients and auxiliaries which facilitate processing of the active compounds into preparations which can be used pharmaceutically. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

In the preferred embodiment, one or more solubilizing agents are included with the insulin agent to promote rapid dissolution in aqueous media. Suitable solubilizing agents include wetting agents such as polysorbates, glycerin and poloxamers, non-ionic and ionic surfactants, food acids and bases (e.g. sodium bicarbonate), and alcohols, and buffer salts for pH control.

Stabilizers are used to inhibit or retard drug decomposition reactions which include, by way of example, oxidative reactions. A number of stabilizers may be used. Suitable stabilizers include polysaccharides, such as cellulose and cellulose derivatives, and simple alcohols, such as glycerol; bacteriostatic agents such as phenol, m-cresol and methylparaben; isotonic agents, such as sodium chloride, glycerol, and glucose; lecithins, such as example natural lecithins (e.g. egg yolk lecithin or soya bean lecithin) and synthetic or semisynthetic lecithins (e.g. dimyristoylphosphatidylcholine, dipalmitoylphosphatidylcholine or distearoyl-phosphatidylcholine; phosphatidic acids; phosphatidylethanolamines; phosphatidylserines such as distearoyl-phosphatidylserine, dipalmitoylphosphatidylserine and diarachidoylphosphatidylserine; phosphatidylglycerols; phosphatidylinositols; cardiolipins; sphingomyelins. In one example, the stabilizer may be a combination of glycerol, bacteriostatic agents and isotonic agents.

II. METHODS OF MAKING THE FORMULATIONS

The injectable formulation contains insulin, a chelator, and a dissolution agent. In a preferred embodiment, the injectable formulation contains insulin, EDTA, Citric acid, saline and/or glycerin.

In one embodiment, the subcutaneous injectable formulation is produced by mixing saline and glycerin, citric acid and EDTA to form a solution and sterilizing the solution (referred to as the "diluent"). The insulin is separately added to sterile water to form a solution, filtered, and a designated amount is placed into each of a number of separate sterile injection bottles. The insulin solution is lyophilized to form a powder and should be stored separately from the diluent to retain its stability. Prior to administration, the diluent is added to the insulin injection bottle. After the predetermined amount of insulin is subcutaneously injected into the patient, the remaining insulin solution may be stored, preferably by refrigeration.

In another embodiment, the insulin is combined with the diluent, pH 4, sterile filtered into multi-use injection vials or cartridges and frozen prior to use.

In a preferred embodiment, the insulin is prepared as an aqueous solution, at pH 7.0, in vials or cartridges and kept at 4° C.

III. METHODS OF USING FORMULATIONS

The formulations may be administered by subcutaneous or intramuscular injection. The formulation is designed to be rapidly absorbed and transported to the plasma for systemic delivery.

Formulations containing insulin as the active agent may be administered to a type 1 or type 2 diabetic patient before or during a meal. Due to the rapid absorption, the compositions can shut off the conversion of glycogen to glucose in the liver, thereby preventing hyperglycemia, the main cause of complications from diabetes and the first symptom of type 2 diabetes. Currently available, standard, subcutaneous injections of human insulin must be administered about one half to one hour prior to eating to provide a less than desired effect, because the insulin is absorbed too slowly to shut off the production of glucose in the liver. Additionally, if given early enough in the progression of the disease, the subcutaneous insulin compositions may be able to slow or stop the progression of type 2 diabetes.

The advantage of the low pH formulation is that it can be mixed with BYETTA® (exenatide), SYMLN® (pramlintide acetate), and LANTUS® (long acting insulin analog), none of which can be mixed with other types of commercially available insulins due to immiscibility and precipitation.

The advantage of the higher pH insulin is that it is more stable during storage than the insulins at lower pH.

The present invention will be further understood by reference to the following non-limiting examples. The following insulins were used in the examples.

HUMULIN® (RHI) is recombinant human insulin. Each mililiter contains 100 units regular recombinant human insulin, 0.22% m-cresol, 1.4-1.8% glycerin, pH 7. This is available commercially from several sources.

HUMALOG® from Eli Lilly (IL), insulin lispro injection, is a recombinant human insulin analog that is a Lys(B28), Pro(B29) human insulin analog, created when the amino acids at positions 28 and 29 on the insulin B-chain are reversed. Each milliliter of IL injection contains insulin lispro 100 units, 16 mg glycerin, 1.88 mg dibasic sodium phosphate, 3.15 mg metacresol, zinc oxide content adjusted to provide 0.0197 mg zinc ion, trace amounts of phenol, and water for injection. Insulin lispro has a pH of 7.0 to 7.8. Hydrochloric acid 10% and/or sodium hydroxide 10% may be added to adjust pH. One unit of IL has the same glucose-lowering effect as one unit of Regular human insulin, but its effect is more rapid and of shorter duration.

NOVOLOG® (IA) is a recombinant insulin analog available from Novo Nordisk A/S. The analog contains a single substitution of the amino acid proline by aspartic acid in position B28, and is produced by recombinant yeast. It is provided in a sterile, aqueous solution containing 100 Units insulin aspart/ml, 16 mg/ml glycerin, 1.50 mg phenol/ml, 1.72 metacresol/ml, 19.6 mg zinc/ml, 1.25 mg disodium hydrogen phosphate dihydrate/ml, 0.58 mg sodium chloride/ml, having a pH of 7.2 to 7.6, adjusted with 10% HCl or NaOH.

VIAJECT™ is a recombinant human insulin formulated with citric acid and EDTA. Viaject 25 U/mL (CE 25-4) contains 25 U/mL regular recombinant human insulin, 1.8 mg/mL Citric acid, 1.8 mg/mL disodium EDTA, 0.82% NaCl (isotonicity) and 3 mg/mL m-cresol. It is provided as an aqueous solution which is stored frozen, or in a two part kit consisting of dry powder insulin and diluent, at least one of which contains citric acid and EDTA. The pH of both reconstituted mixture and frozen solution is approximately pH 4. The reconstituted powder is what was used in the examples. Viaject 100 U/mL (CE 100-4) contains 100 U/mL regular recombinant human insulin, 1.8 mg/mL citric acid, 1.8 mg/mL disodium EDTA, 22 mg/mL glycerin, 3 mg/mL m-cresol. This is also provided either as a frozen aqueous solution or two part kit consisting of dry powdered insulin and diluent. The pH of both of the reconstituted mixture and frozen solution is approximately 4. Only the frozen aqueous solution was used in the analytical centrifuge data and malvern. Viaject 100 U/mL (CE 100-7) contains 100 U/mL regular recombinant human insulin, 1.8 mg/mL citric acid, 1.8 mg/mL disodium EDTA, 22 mg/mL glycerin, 3 mg/mL m-cresol. This is provided as an aqueous solution having a pH of about 7.4, which can be stored at 4° C. This was used in the swine study. VIAject with acid salts (CSE 100-7) is made with 1.8 mg/mL of both EDTA and trisodium citrate in water, with 100 U/mL insulin and glycerin (22 mg/mL). The final pH is adjusted to 7.4 with sodium hydroxide. This was used in the final example for malvern information.

Example 1

In Vitro Comparison of Uptake and Transport of Insulin Using Epithelial Cell Transwell Assay as a Function of Dissolution Agent Materials and Methods Oral epithelial cells were grown on transwell inserts for two weeks until multiple (4-5 layer) cell layers had formed, as shown in FIG. 2. The transport studies were conducted by adding the appropriate solutions to the donor well and removing samples from the receiver well after 10 minutes. Solutions consisted of water, +/−EDTA (0.45 mg/ml), NaCl (0.85% w/v), 1 mg/ml insulin and a sufficient amount of acid to maintain the pH at 3.8. Insulin amounts in the receiver wells were assayed using ELISA.

Results

Figure 3A:
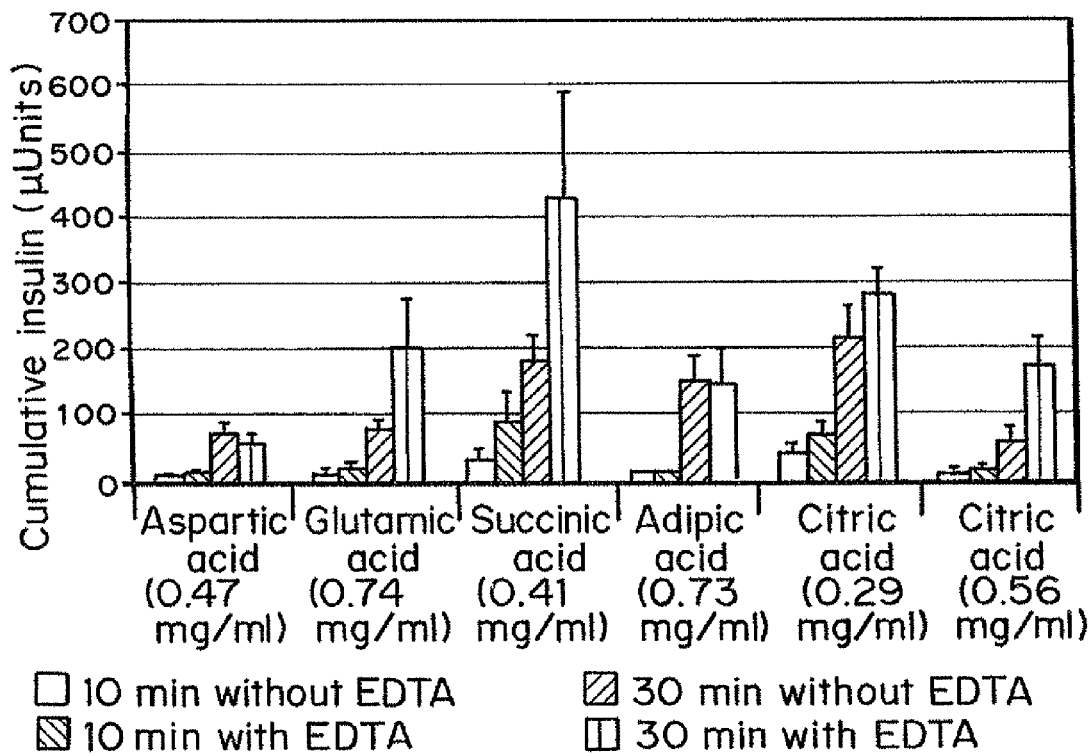
FIGS. 3a and 3b are graphs comparing in vitro insulin transport (cumulative insulin in microunits) through oral epithelial cells in the transwell system of FIG. 2, with and without 0.45 mg EDTA/ml, as a function of acid selected as dissolution agent. EDTA was constant at 0.45 mg/mL while the acid concentrations were varied as follows.
Figure 3B:
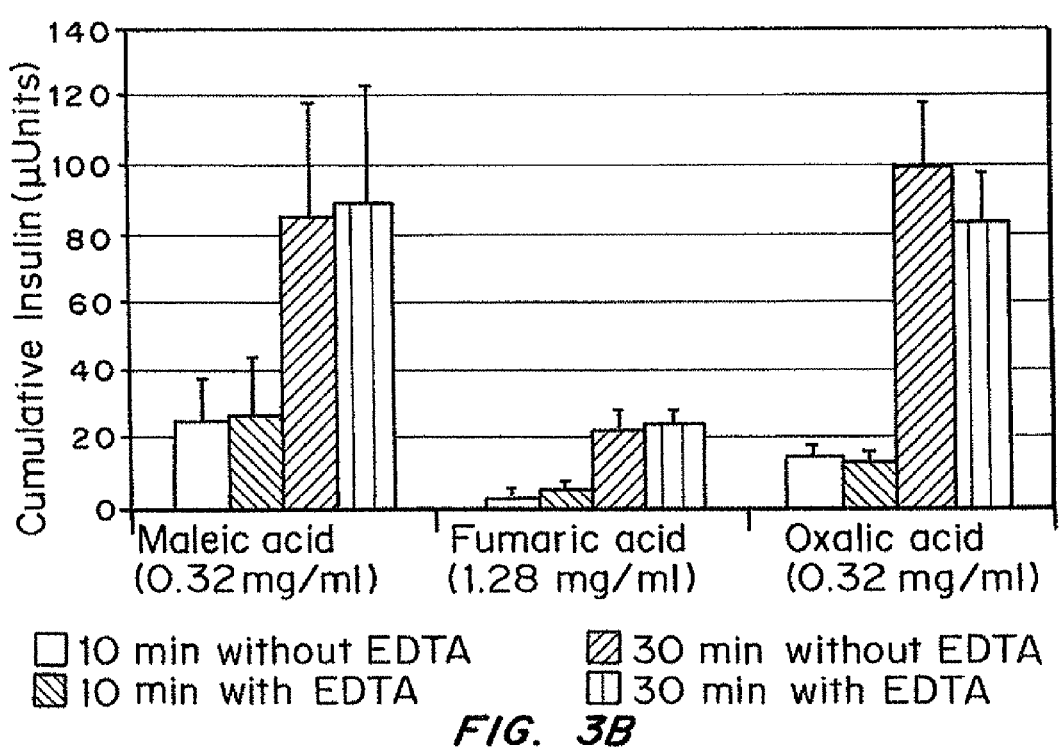

The results shown in FIGS. 5a and 3b demonstrate that some acids are more effective at enhancing uptake and transport of insulin through epithelial cells. These can be readily tested and compared to the results obtained using HCl, thereby providing a standard against which any acid can be tested and determined to be a dissolution agent (i.e., enhancing uptake and transport relative to HCl) or not.

Results obtained with acids with pH range of 3.2-3.8 are grouped in FIG. 3a. Stronger acids (H<3) are grouped in FIG. 3b.

The results establish that the choice of acid with the same concentration of chelator has a substantial effect on the transport of insulin through cell culture. The preferred acid is citric acid.

Example 2

In Vitro Comparison of Uptake and Transport of Insulin Using Epithelial Cell Transwell Assay as a Function of Concentration of Dissolution Agent Materials and Methods The materials and methods of Example 1 were used with different concentrations of reagents. In the study, equimolar concentrations of acid and chelator were added. Solutions consisted of water, +/− EDTA (0.56 mg/mL), NaCl (0.85% w/v), 1 mg/mL insulin and an acid: Aspartic acid (0.20 mg/mL), Glutamnic acid (0.22 mg/mL) or citric acid (0.20 mg/ml). Citric acid was tested at a higher concentration of 1.8 mg/mL with and without chelator. This data is shown at two time periods, 10 and 30 minutes, post dosing of cell donor chambers.

Results

Figure 4A:
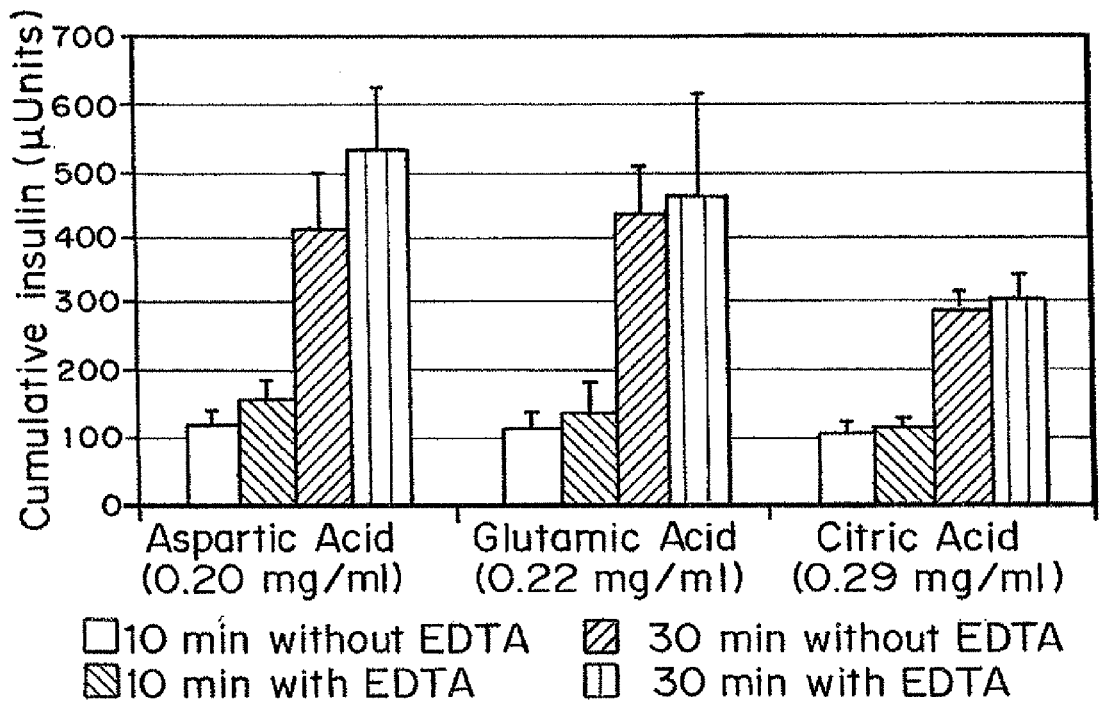
FIGS. 4a and 4b are graphs of in vitro insulin transport (cumulative insulin in microunits) through oral epithelial cells in the transwell system shown in FIG. 2, comparing different dissolution agents, with and without 0.56 mg EDTA/mL and acids at the following equimolar ($1.50 \times 10^{-3}$ Mol) concentrations: Aspartic acid (0.20 mg/mL), Glutamic acid (0.22 mg/mL) and citric acid (0.29 mg/ml) (FIG. 4a) and Citric acid at 1.80 mg/mL (FIG. 4b). Two time periods (10 and 30 min.) were selected for comparative analysis.

The results obtained with Aspartic acid (0.20 mg/mL), Glutamic acid (0.22 mg/mL) or citric acid (0.29 mg/ml) are shown in FIG. 4a. In this case, there was no significant difference seen with the addition of the chelator.

Figure 4B:
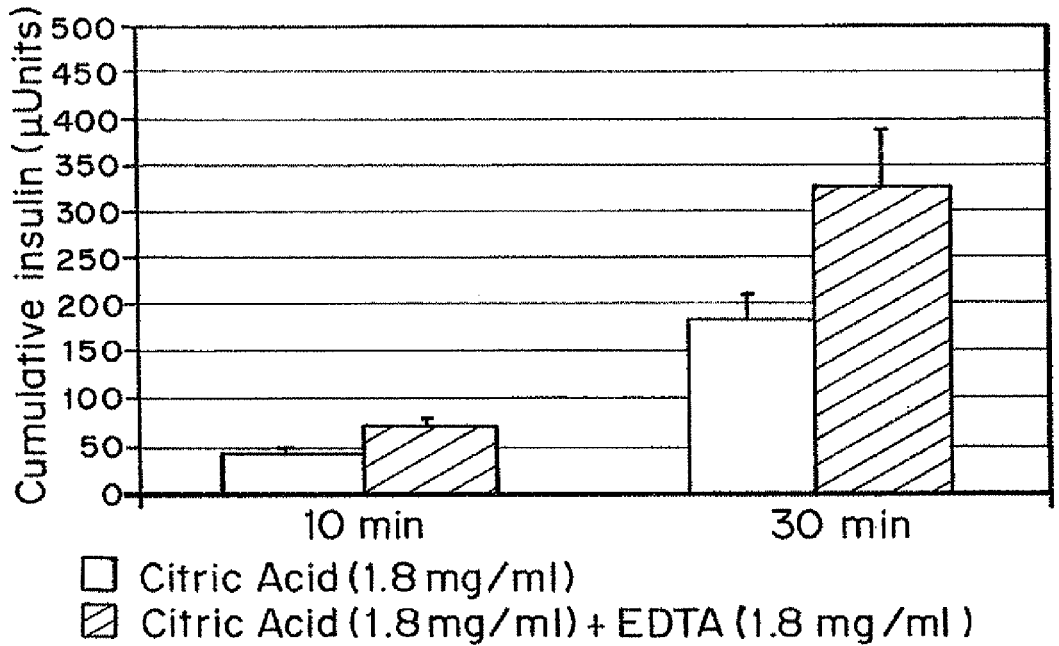

In contrast, the study using a higher concentration of Citric acid, at 1.80 mg/mL, does show a significant increase (t-test comparison, one sided) upon addition of the chelator to the solution. See FIG. 4b. This demonstrates that concentration of both components is important in optimizing uptake and transport.

Example 3

In Vitro Comparison of Uptake and Transport of Insulin Using Epithelial Cell Transwell Assay as a Function of Chelator Materials and Methods Oral epithelial cells were grown on transwell inserts for two weeks until multiple (4-5 layer) cell layers had formed. The transport studies were conducted by adding the appropriate solutions to the donor well and removing samples from the receiver well after 10, 20 and 30 minutes.

The solutions were prepared immediately before the transwell experiments in the following way: Citric acid at 1.8 mg/ml was dissolved in 0.85% w/v saline and then one of the following chelators was added to this solution at the concentration shown: EDTA at 1.80 mg/ml, EGTA at 1.84 mg/ml, DMSA at 0.88 mg/ml and TSC at 1.42 mg/ml. Because CDTA was used in its liquid form, citric acid was added directly to the CDTA. In each of these cases, the concentration of chelator was constant at $4.84 \times 10^{-3}$ moles.

Insulin was then added at 1 mg/ml and the pH was re-adjusted to 3.8 if necessary. A control set of samples using only HCl for pH adjustment are included for comparison. Transwell experiments were done by adding 0.2 ml of each solution to the donor wells.

Insulin amounts in the receiver wells were assayed using ELISA.

Results

Figure 5:
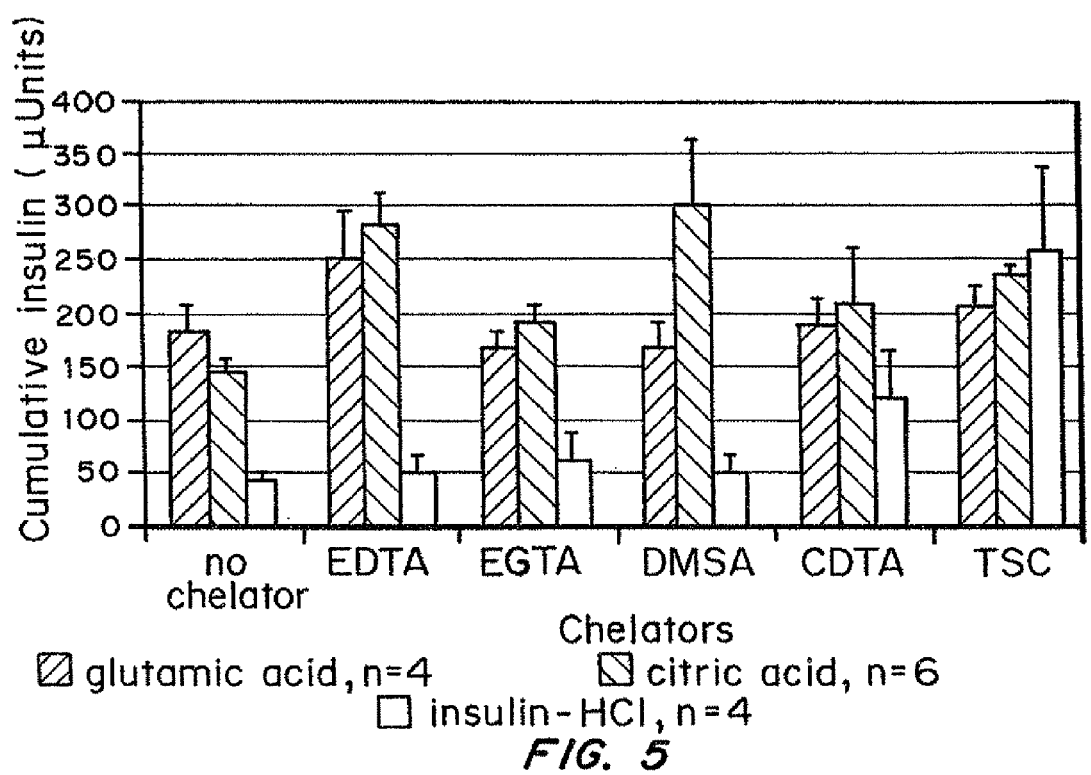
FIG. 5 is a graph of in vitro insulin transport through oral epithelial cells using the transwell system of FIG. 2 to compare efficacy of different chelators.

A graph of 30 minute insulin data is shown in FIG. 5. There was significantly more insulin delivered through the cells when citric or glutamic acid was used, except as compared to results obtained with TSC (trisodium citrate). In the case of TSC, HCl was used for pH adjustment. The adjustment of pH generated citric acid, explaining these results.

As demonstrated by these results, enhancement of uptake and transport is dependent on the choice of chelator.

Example 4

Preclinical Evaluation of Chelators in a Citric Acid Based Insulin Formulation in Swine Materials and Methods In concert with a published study, A. Plum, H. Agerso and L. Andersen. Pharmacokinetics of the rapid-acting insulin analog, insulin aspart, in rats, dogs, and pigs, and pharmacodynamics of insulin aspart in pigs. Drug Metab. Dispos., 28(2):155-60 (2000), it was determined that the elimination half life was a good determinant of the absorption of insulin, since a delay in the elimination implies slower absorption from the injection site. Therefore, a non-compartmental analysis of a miniature swine study was performed to examine PK and PD parameters, in particular elimination half life.

Diabetic swine were injected subcutaneously with one of four formulations of insulin. Three formulations contained a chelator (EDTA, EGTA or TSC) and fourth control contained only regular human insulin RHI, no chelator. Citric acid (1.8 mg/ml) was used as the acid in all the chelator formulations, and NaCl and m-cresol were added for isotonicity and formulation sterility in all cases. The chelators were all at the same molar concentration of $4.84 \times 10^{-3}$ moles.

Swine were fasted overnight, and subcutaneously administered a dose of 0.125 U/kg human insulin containing EDTA (n=3) or 0.08 U/kg human insulin containing EGTA or TSC (n=2). Doses were reduced due to extreme blood glucose lowering with the higher dose. Blood glucose and insulin levels were determined at all timepoints, to 8 hours post dose.

Pharmacokinetic modeling was performed with Win Nonlin, using a noncompartmental model with uniform weighting. Elimination half lives were compared in Table 1:

TABLE 1

Comparison of Blood Insulin in Swine as Function of Chelator

| Insulin | Half life "lamda z" (min. +/− sd) Terminal half life |
|---|---|
| RHI/No chelator | 120 |
| Insulin/EDTA | 39.1 +/− 15.8 |
| Insulin/EGTA | 37.5 +/− 8.0 |
| | 30.1 +/− 9.0 |

The elimination half life of regular human insulin (120 min.) in this pilot study in swine was consistent with that seen in the literature and was used as a test point to validate the data. As this is considerably longer than following intravenous administration, this confirms there is continued slow absorption from the injection site following injection. The chelators in the citric acid formulation clearly show a reduction in this parameter, demonstrating that these three chelators are effective in enhancing the absorption of regular human insulin, although to different degrees.

Example 5

Comparison of EDTA-Citric Acid Insulin Formulation to Regular Human Insulin in Human Clinical Trial Materials and Methods The aim of this study was to evaluate the pharmacodynamic (PD) properties of a test formulation containing insulin in combination with citric acid and EDTA, "CE 25-4". Five euglycemic glucose-clamps (Biostator; target blood glucose 90 mg/dl) were performed in 10 fasting healthy volunteers (mean age 40 (20-62 years range); BMI 22.5 (19.2-24.9) kg/m²). Using a cross-over design with a fixed treatment order, 12 IU Regular insulin and 12 IU of CE insulin formulation were injected subcutaneously in the abdominal region.

Results

Figure 6:
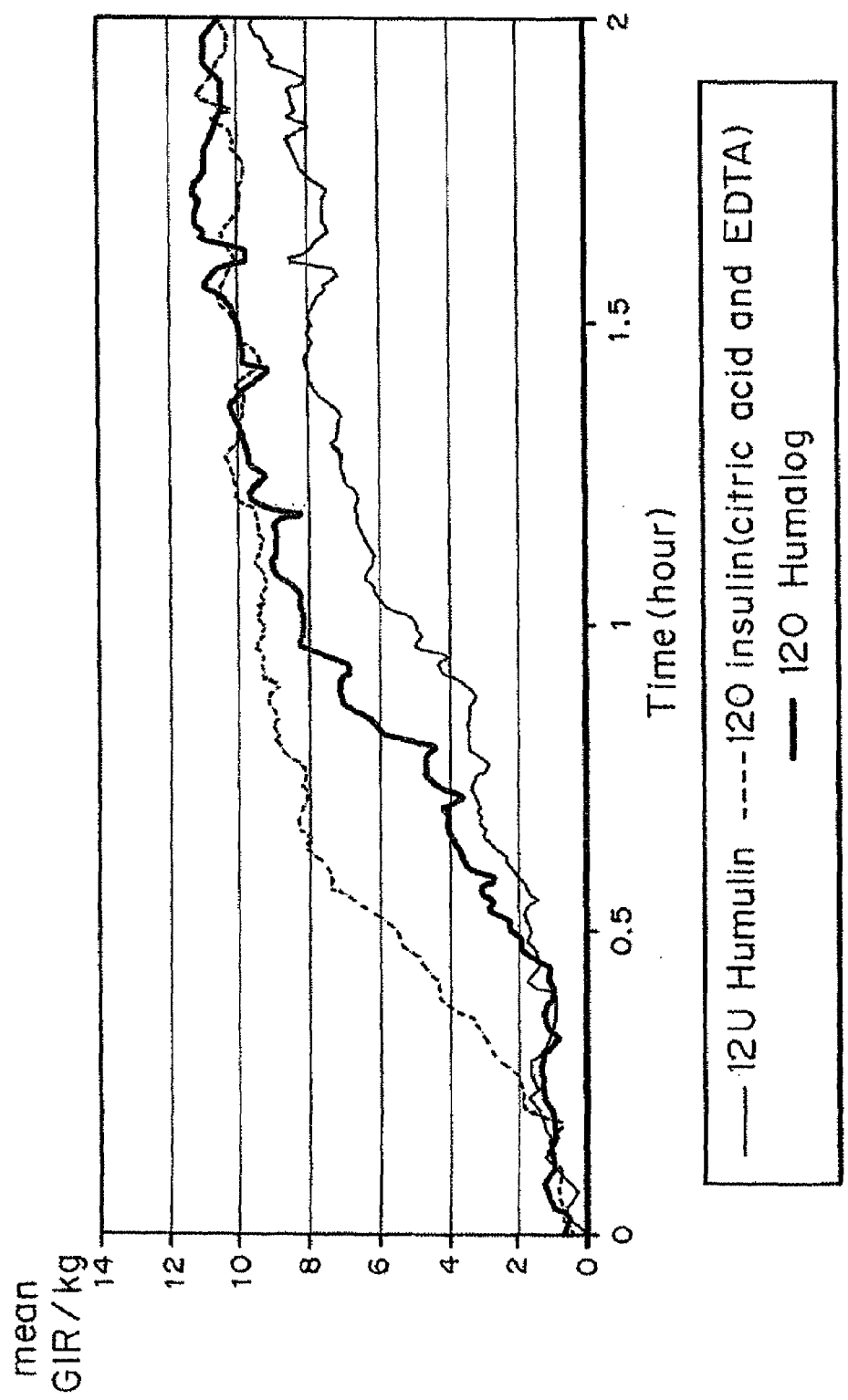
FIG. 6 is a graph of the in vivo pharmacodynamic effect of insulin prepared with citric acid and EDTA (12 U) in human subjects, compared to IL (12 U) and RHI (12 U), measured as mean glucose infusion rate (GIR)/kg.
Figure 7:
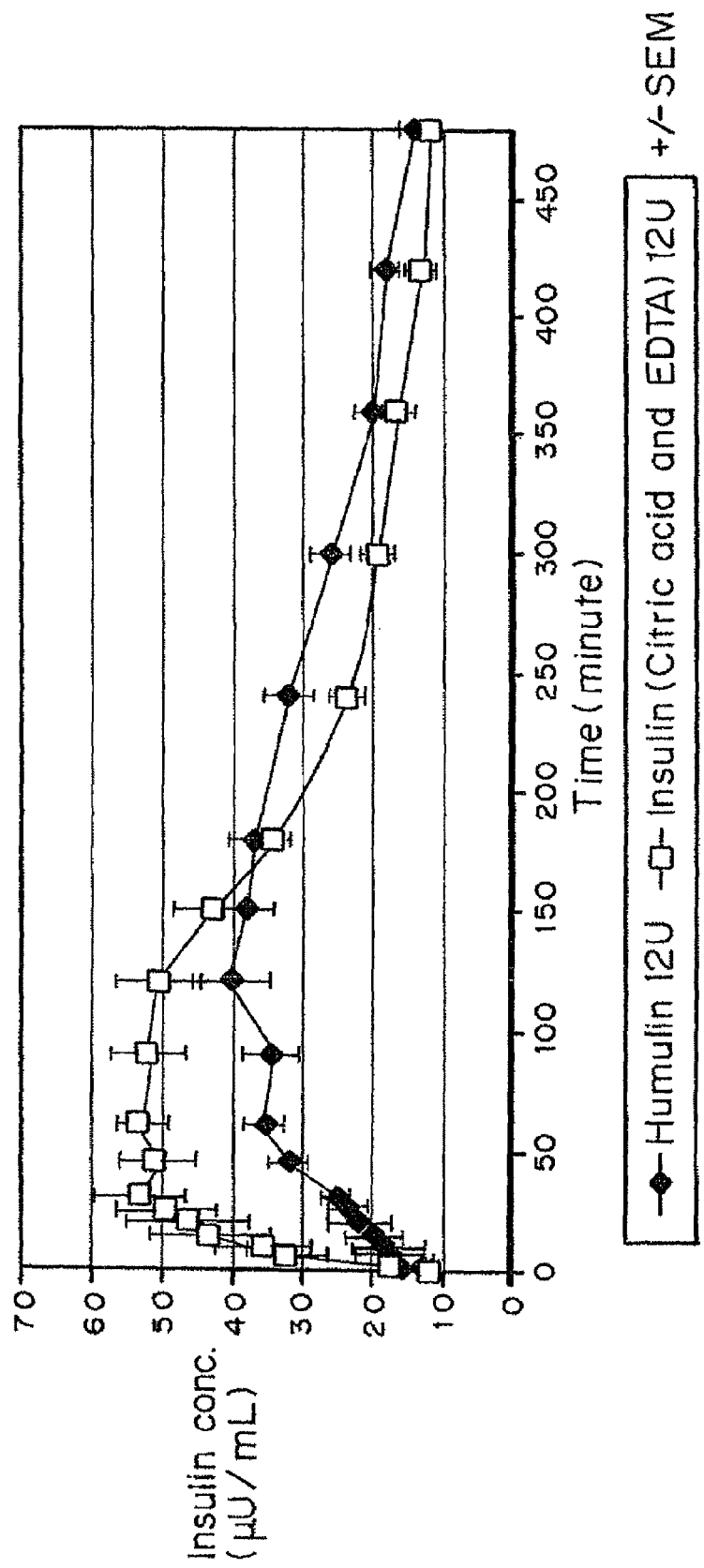
FIG. 7 is a graph of the in vivo pharmacokinetic effect of insulin prepared with citric acid and EDTA in humans, compared to RHI, insulin concentration (microUnits/ml) over time (minutes). Mean values (±SEM, n=10). Insulin dose was 12 U/subject.

The results are shown in FIGS. 6 and 7. SC injection of CE 25-4 resulted in a time-action profile that produced a significantly more rapid rise in glucose consumption regular human insulin (FIG. 6). The mean pharmacokinetic data confirm the PD results (FIG. 7).

This study shows that addition of citric acid and EDTA to regular human insulin improves the rate of absorption of insulin as demonstrated by a faster time to maximal concentration (FIG. 7) and a more rapid onset of action (FIG. 6) compared to regular human insulin alone.

Example 6

Pharmacokinetics and Pharmacodynamics of CE Insulin, Insulin Lispro and Regular Human Insulin when Injected Subcutaneously Immediately Before a Meal in Patients with Type 1 Diabetes Background and Aims:

The aim of this study was to determine the action of CE 25-4, RHI, and IL on postprandial blood glucose (BG) excursions after a standard meal in patients with Type 1 diabetes.

Materials and Methods

BG of 9 patients (5 males and 4 females; age 40±10 yrs, BMI 24.0±2.0 kg/m$^2$) were stabilized by means of a glucose clamp (target BG 120 mg/dl) prior to meal ingestion. The glucose infusion was turned off prior to the standard meal and insulin dosing. Using a cross-over study design with fixed treatment order, the same patient specific dose of VIAject™ (CE25-4) IL or RHI was injected s.c. immediately before the meal. Subsequently, postprandial glucose excursions were continuously monitored for 8 hours and glucose infusion was re-initiated if BG was less than 60 mg/dl. Plasma insulin levels were determined throughout the study.

Results

The results shown in Table 2 as the mean plus or minus standard deviation compare insulin Tmax after subcutaneous injection to type 2 diabetic patients after a meal, regular human insulin, insulin plus citric acid and EDTA (CE) and lispro. The results in Table 3 compare blood glucose for the same test subjects.

TABLE 2

Comparison of Insulin Tmax (min)

| Pharmacokinetics | RHI | IL | (CE25-4) |
|---|---|---|---|
| Ins Tmax (min) | 143 ± 29* | 62 ± 37 | 43 ± 36* |

*p < .001, paired t-test

TABLE 3

Comparison of Insulin Pharmacokinetics Blood Glucose

| Pharmacodynamics (0-180 min.) | RHI | IL | CE 25-4 |
|---|---|---|---|
| BG TMax (min.) | 93 ± 56* | 47 ± 28 | 41 ± 26* |
| BG Max (mg/dL) | 185 ± 44 | 158 ± 33 | 157 ± 27 |
| BG Min (mg/dL) | 103 ± 21 | 73 ± 31 | 87 ± 24 |
| BG Max-BG Min (mg/dL) | 82 ± 30 | 84 ± 11* | 70 ± 18* |

*p < 0.05, paired t-test

Figure 8:
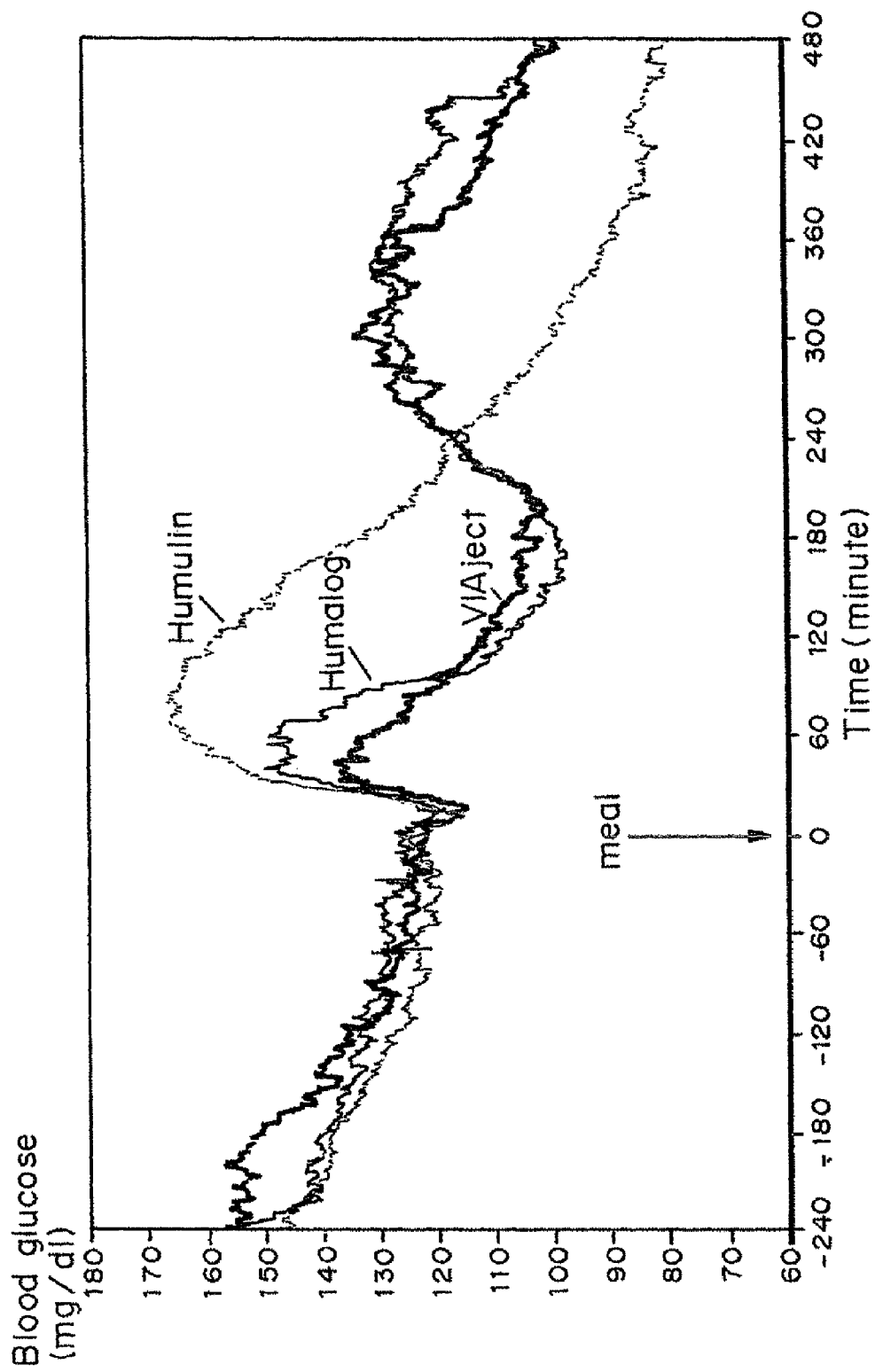
FIG. 8 is a graph of the in vivo pharmacodynamics of insulin prepared with citric acid and EDTA in 16 diabetic type 2 patients; compared to RHI and IL, plotting blood glucose (mg/dl) over time (minutes). The dosage used in the patient trial was patient specific, adjusted for each patient based on their current insulin therapy.

The total number of hypoglycemic events (hours requiring glucose infusion) 3 to 8 hours post injection were 13 with RHI, 1 with IL and 4 with the CE 25-4 formulation. The mean total amount of glucose infused to prevent hypoglycemia during this time was six times higher for RHI and twice as much for IL than with CE 25-4. The areas above and below the normal glycemic target zone (BG AUC above 140 and below 50 mg/dL) summed for all patients per group was 81,895 for RHI 57,423 for IL and 38,740 mg/dL*min for CE 25-4. The mean blood glucose levels are shown in FIG. 8.

CE 25-4 was the fastest in reversing the rise in blood glucose following the standard meal. Patients treated with CE 25-4 experienced reduced post prandial glucose excursions. In contrast, RHI had the highest glucose excursion, which is consistent with its slower absorption rate. Variability of the glucose levels (mean difference between maximal and minimal values) was significantly less for CE 25-4 than IL, demonstrating the better glycemic control of CE 25-4 in these patients with Type 1 diabetes.

Example 7

Characterization of Size of Insulins by Light Scattering

CE 100-4 has a very rapid onset of action in patients. To understand the basis for the rapid absorption profile, in vitro experiments were performed with CE 100-4 in comparison to other commercially available recombinant human insulins and rapid acting analogs of insulin. Light scattering techniques were applied to the original products as well as a dilution series in synthetic extracellular fluid buffer. The results show that unlike regular recombinant insulin and the rapid acting analogs, CE 100-4 reduces in size to approximately that of a dimer after a 1:3 dilution, which is consistent with its rapid absorption profile.

Materials and Methods

In order to elucidate the mechanism of this rapid onset of action, in vitro experiments were designed to study the effect of dilution of the traditional formulation in a synthetic extracellular fluid buffer as a means to simulate what naturally occurs following subcutaneous injection. A light scattering technique was used to assess the mean size distribution (nm). Commercial rapid acting or prandial insulin formulations that were used for comparison in these in vitro experiments were: IL, IA, RHI and CE 100-4. For size comparison, standard preparations of monomeric (pH 2.0) and hexameric zinc insulins (pH 7) were used for standards.

Commercial insulins were characterized for size with the Zetasizer nano (Malvern Inst, UK). One mL samples were placed in a glass cuvette and were analyzed to determine a mean average volumetric size distribution (nm) of the insulin in solution. The mean of 3 samples (each sample had several runs) was used as a basis for comparison. Following the initial fall strength analysis, a dilution series was performed from 1:2 to 1:16 in buffer having similar pH and buffering capacity of extracellular fluid (ECF, 0.7 mN MgCl$_2$, 1.2 mM CaCl$_2$, 0.2 mM KCl, 0.5 mM Na$_2$SO$_4$, 104 mM NaCl, 28.3 mM NaHCO$_3$). The mean size was determined for all dilutions with each of the commercially available insulins and CE 100-4, to understand the monomer/dimer/hexamer size distribution for each formulation.

Insulins

RHI, IL, IA, and CE 100-4.

Diluents

ECF, 0.7 mM MgCl$_2$, 1.2 mM CaCl$_2$, 2 mM KH$_2$PO$_4$, 2 mM KCl, 0.5 mM Na$_2$SO$_4$, 104 mM NaCl, 28.3 mM NaHCO$_3$ in sterile water.

Results

In the size measurement studies, undiluted CE 100-4 is larger than IL, IA and RHI. However, with a 1:3 dilution, the mean size of CE 100-4 was reduced by 2 nm to the monomeric/dimeric size while the other insulins studied remained at the hexameric size of approximately 5 nm. CE 100-4 but not IL, IA and RHI was further reduced with increased dilution. Undiluted RHI appears smaller but grows in size to greater than 5 nm once diluted 1:1 and remains in this size range out to a dilution of 1:16.

Undiluted CE 100-4 initially appears larger than the other insulins studied, possibly due to citric acid and EDTA being weakly attracted to the surface, which may serve to further increase the rate of absorption from subcutaneous sites by masking the surface charge. Charge can be an impediment to absorption. Shortly after subcutaneous administration, as the injected material is diluted by ECF, CE 100-4 has a smaller mean size than rapid acting insulin analogs and RHI at identical dilutions.

Example 8

Analytical Ultracentrifugation of Insulin

Materials and Methods

A set of experiments was developed using analytical ultracentrifugation, which determines an estimate of the weight averaged sedimentation coefficient (Svedbergs 20° C., water S(20,w)), which is proportional to the buoyant effective molar weight. The procedure for this analysis was somewhat different than the light scattering size determination. First, each sample is diluted with a diluent that is identical in composition to that of the commercial product. To obtain this, a Centriprep® Ultracel-3 membrane filter unit (Millipore Inc, MA, USA) with a 3 kDa MW cutoff was used to separate the insulin from the diluent. The original diluent was recovered and analyzed for the presence of any insulin content. Confirmed insulin free diluents were used to dilute the commercial product.

These first data sets were used to characterize the insulin as either a stable single species, or one that changes from hexamer, dimer, monomer in its own diluent. Two sets of data were derived using analytical ultracentrifugation. The first set of data was obtained by dilution with exactly the diluent of the formulation. In the cases of the commercial preparations, this was obtained by centiprep tubes which separate the insulin or analogue from the diluent. The filtrate was checked for protein content and post confirmation was used for the diluent in the first round of experiments.

The second set of samples was prepared substituting ECF buffer instead of diluent. In order for this to work, the most concentrated sample was diluted first with ECF 1:2. Further dilutions were then done with ECF. In the case of CE 100-4, the initial dilution with ECF was 1:4 to assure that the isoelectric point was crossed to eliminate any precipitated matter. These experiments were intended to mimic the post subcutaneous injection environment.

The values obtained for the weight average sedimentation coefficient for each loading concentration, corrected to standard conditions, is given in the table below. Velocity analysis was conducted at 20° C. and 55,000 RPM using interference optics with a Beckman-Coulter XL-analytical ultracentrifuge. Double sector synthetic boundary cells equipped with sapphire windows were used to match the sample and reference menisci. The rotor was equilibrated under vacuum at 20° C. and after a period of approximately 1 hour at 20° C. the rotor was accelerated to 55,000 RPM. Interference scans were acquired at 60 second intervals for 5 hours Several analytical programs were run on the data (DcDt+ vers. 2.1.02, and Sedfit, vers 11.3b3) to extract information specific to each sample. The data from the Sedfit program is shown in the results below. DcDt is a model independent, sedimentation coefficient distribution g(s*) which uses the time derivative of the concentration profile. If there is no shift to higher values of S with an increase in concentration, it is strong evidence that there are no reversible reactions occurring (i.e. monomer, dimer hexamer). If the size and shape change on dilution (shifting from hexamer to dimer to monomer), it is not possible to determine an estimate of the molecular weight, but useful information can be obtained from the Sedfit program on the sedimentation coefficient S(w). In addition, this program produces a direct boundary model for the individual data sets using a model based numerical solution to the Lamm equation. [3]It plots the continuous sedimentation coefficient c(s) versus sedimentation coefficient (s) to produce curves that describe relative sizes of the sedimenting species.

Dilution of Each Insulin with Insulin-Specific Diluent:

A. RHI

RHI was submitted for analysis by sedimentation velocity ultracentrifugation. The estimated stock concentration was 3.745 mg/ml. The diluent was as described above.

The following physical constants were calculated from the amino acid compositions for the protein using the program Sednterp.[5]

RHI: $MW_{seq}$=5792 Da. $N_{20°}$=0.726 ml/g

The diluent density and viscosity were calculated to be 1.00231 g/ml and 0.01041 poise at 20° C., respectively, using Sednterp.

Results

Figure 9A:
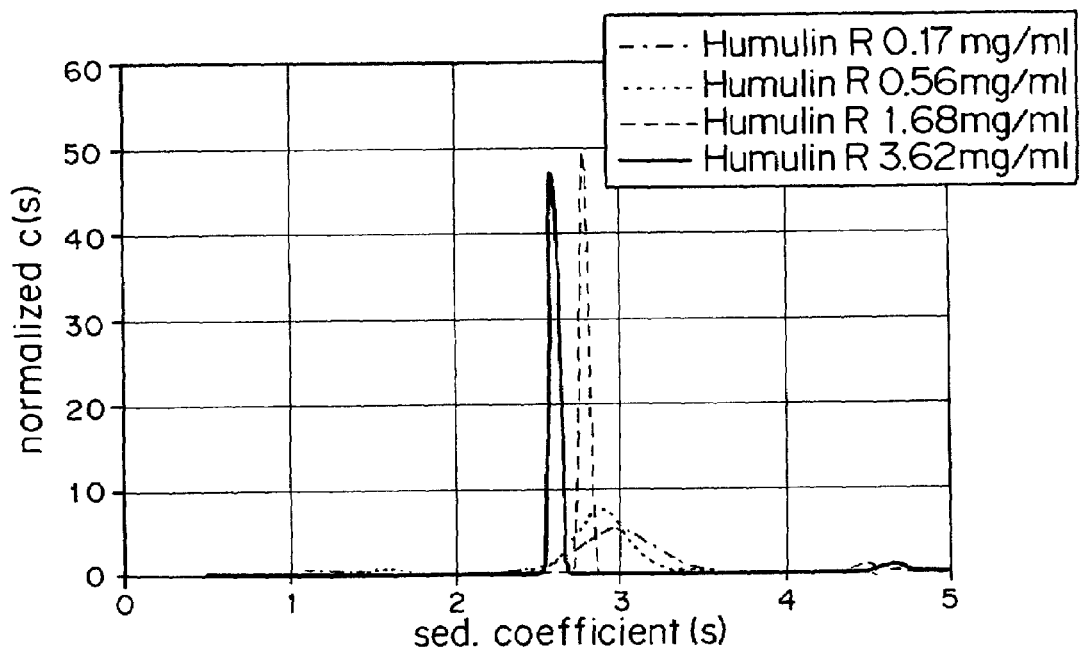
FIG. 9A is a graph of the sedimentation coefficients of RHI at concentrations of 0.17, 0.51, 1.68, and 3.62 mg/ml.

FIG. 9A shows a plot of the c(s) distributions normalized to the loading concentration of RHI™. The data shown for the normalized c(s) plot is consistent with the g(s*) data from the DcDt+. There is a marked shift to lower values of S in the sedimentation with an increase in concentration.

The values obtained for the weight average sedimentation coefficient for each loading concentration, corrected to standard conditions, is given in the table below.

| Cell # | S (20, w) (Svedbergs) | Conc. (mg/ml) |
| --- | --- | --- |
| 1 | 3.05 | 0.168 |
| 2 | 3.00 | 0.561 |
| 3 | 3.00 | 1.678 |
| 4 | 2.84 | 3.624 |

Conclusion:

These analyses indicate that RHI under the conditions of the experiment exists primarily as a hexamer. There is a small amount of slower sedimenting material present in the lower concentration samples, as well as what appears to be dimers of the hexamers.

B. IL

Materials and methods were as described above.

Results

Figure 9B:
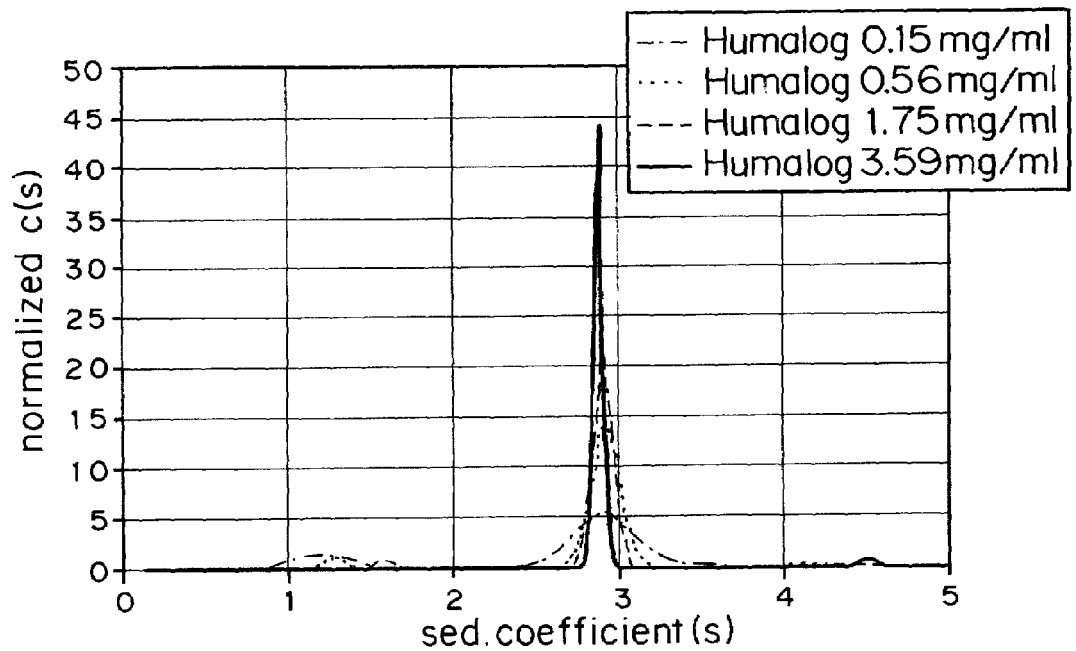
FIG. 9B is a graph of the sedimentation coefficients of IL at concentrations of 0.15, 0.56, 1.75, and 3.59 mg/ml.

FIG. 9B is a plot of the weight average sedimentation coefficients for each concentration. The protein dissociates upon dilution. In addition, there appears to be a small amount (<5%) of faster sedimenting species that is probably a dimer of the hexamer.

The values obtained for the weight average sedimentation coefficient for each loading concentration, corrected to standard conditions, is given in the table below.

| Cell # | S (20, w) (Svedbergs) | Conc. (mg/ml) |
| --- | --- | --- |
| 1 | 2.78 | 0.151 |
| 2 | 3.02 | 0.558 |
| 3 | 3.09 | 1.755 |
| 4 | 3.10 | 3.595 |

Conclusions:

These analyses indicate that the protein sample, IL, under the conditions of this experiment, exists primarily as a hexamer. There is evidence of the dissociation of IL upon dilution, and there is a small amount of what appears to be dimers of the hexamers present. The concentrations studied were approximately 30 μm, 100 μm, 300 μm, and 600 μm (monomer units).

C. IA

Materials and Methods are as described above.

Results

Figure 9C:
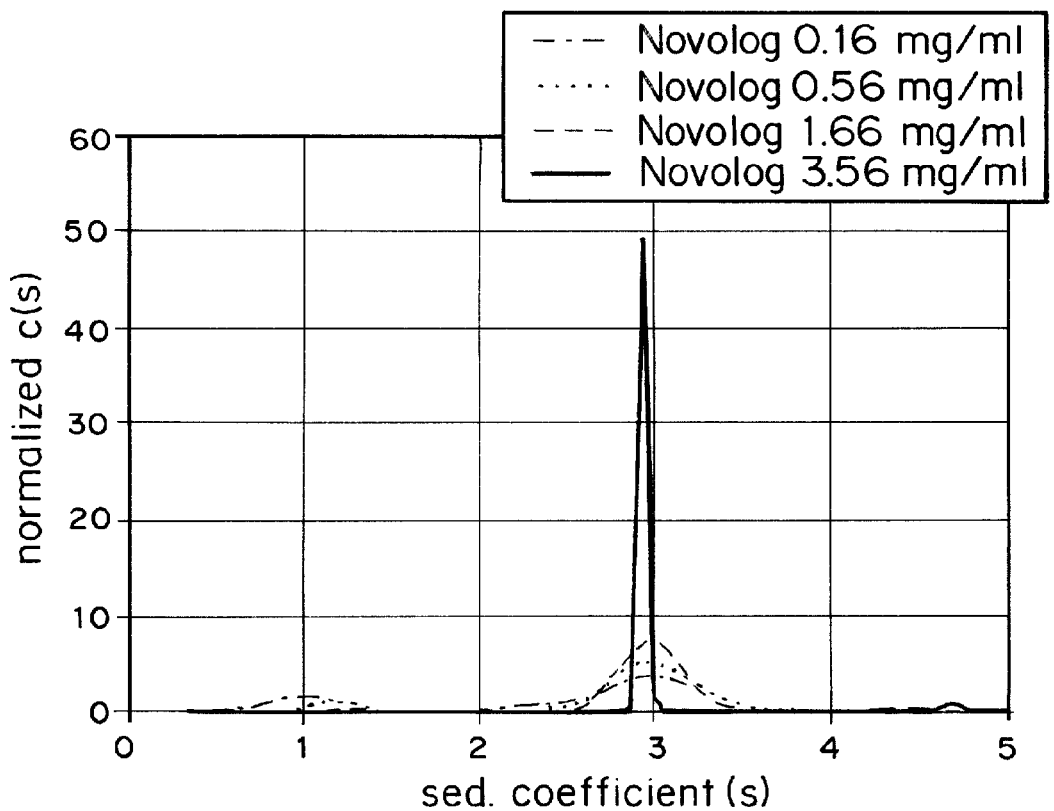
FIG. 9C is a graph of the sedimentation coefficients of IA at concentrations of 0.16, 0.56, 1.66, and 3.56 mg/ml.

FIG. 9C shows a plot of the c(s) distributions normalized to the loading concentration. The data shown for the normalized c(s) plot is consistent with the g(s*) data from DcDt+. The c(s) curves at low concentrations show a contribution of a smaller species (monomer) which decreases as the concentration is increased. There is also a slight shift to lower values of S in the sedimentation with an increase in concentration. There appears to be a small amount (<5%) of faster sedimenting species that is probably a dimer of the hexamer.

The values obtained for the weight average sedimentation coefficient for each loading concentration, corrected to standard conditions, is given in the table below.

| Cell # | S (20, w) (Svedbergs) | Conc. (mg/ml) |
|---|---|---|
| 1 | 2.72 | 0.158 |
| 2 | 3.05 | 0.561 |
| 3 | 3.19 | 1.655 |
| 4 | 3.14 | 3.563 |

Conclusions:

These analyses indicate that IA, under the conditions of this experiment, exists primarily as a hexamer. There is evidence of the dissociation of IA upon dilution, and there is a small amount of what appears to be dimers of the hexamers present. The concentrations studies were approximately 30 μm, 100 μm, 300 μm, and 600 μm (monomer units).

D. CE-100 4

Materials and Methods were as described above.

Results

Figure 9D:
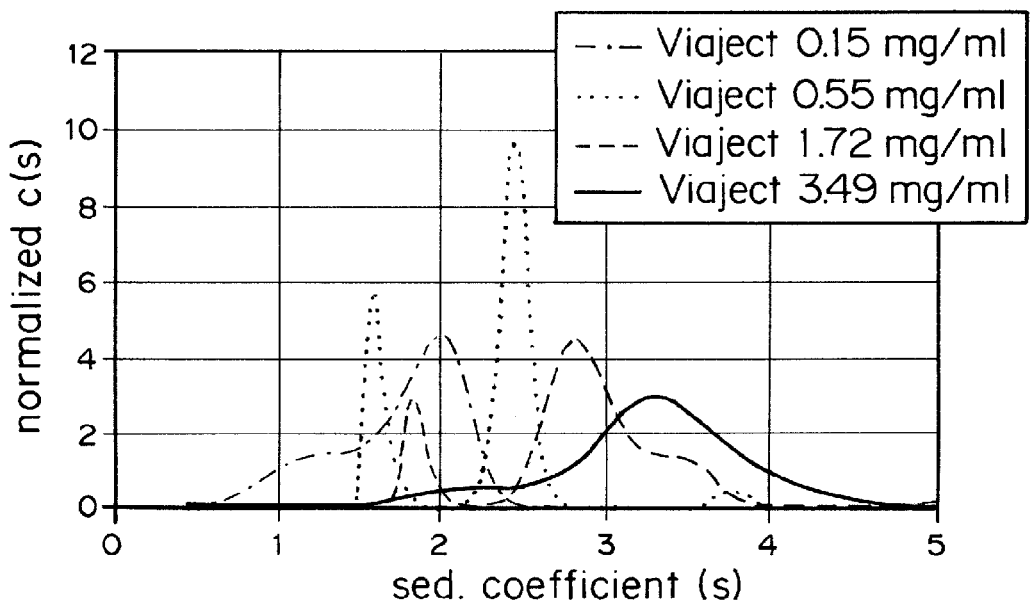
FIG. 9D is a graph of the sedimentation coefficients of CE100-4 at concentrations of 0.15, 0.55, 1.72, and 3.48 mg/ml.

The databases for CE-100 4 were analyzed using Sedfit and the c(s) model. Strictly speaking this model is only applicable to non-interacting mixtures but in the case of interacting species it can still yield an idea of which species are present in solution. FIG. 9D shows a plot of the c(s) distribution normalized in the loading concentration. The c(s) plot is consistent with the g(s*) data from DcDt+ in that there is a marked shift towards lower S values upon dilution. The c(s) plots from the higher concentrations clearly show that CE 100-4 may be larger than a hexamer. The value obtained for the weight average sedimentation coefficient for each loading concentration, corrected to standard conditions, is given in the table below.

| Cell # | S (20, w) (Svedbergs) | Conc. (mg/ml) |
|---|---|---|
| 1 | 1.85 | 0.153 |
| 2 | 2.41 | 0.548 |
| 3 | 3.05 | 1.722 |
| 4 | 3.56 | 3.484 |

Conclusions:

These analyses indicate that the protein sample, CE 100-4, under the conditions of this experiment, exists in an equilibrium between monomers, dimers, hexamers, and possibly larger oligomers. The concentrations studies were approximately 30 μm, 100 μm, 300 μm, and 600 μm (monomer units).

Dilution with ECF Buffer:

Commercial preparations were first diluted 1:2 with ECF, with the exception of CE 100-4, which was diluted 1:4. This had to be treated differently to avoid precipitation through the isoelectric point, since it starts at pH 4. The other commercial insulins were already at pH 7, so initial dilution was to 1:2.

A. RHI

RHI was submitted for analysis by sedimentation velocity ultracentrifugation. The estimated stock concentration was 1.87 mg/ml after dilution with an equal volume of the supplied ECF.

The following physical constants were calculated from the amino acid composition for the protein using the program Sednterp.[5]

RHI: $MW_{seq}$=5792 Da, $N_{20°}$=0.726 ml/g

The diluent density and viscosity were calculated to be 1.00273 g/ml and 0.01043 poise at 20° C., respectively, using Sednterp.

The dilution scheme, using the stock solution, for the three cells used in the analysis is shown in the following table:

| Cell # | Vol. Stock (μl) | Vol. Buffer (μl) | Est. Conc. (mg/ml) |
|---|---|---|---|
| 1 | 45 | 405 | 0.19 |
| 2 | 150 | 300 | 0.62 |
| 3 | 450 | — | 1.87 |

Sedfit, version 11.71, was used with direct boundary modeling program for individual data sets using model based numerical solutions to the Lamm equation.[3]

Continuous sedimentation coefficient distribution, c(s), model was calculated. The c(s) distribution plots are sharpened, relative to other analysis methods, because the broadening effects of diffusion are removed by use of an average value for the frictional coefficient.

Results

Figure 10A:
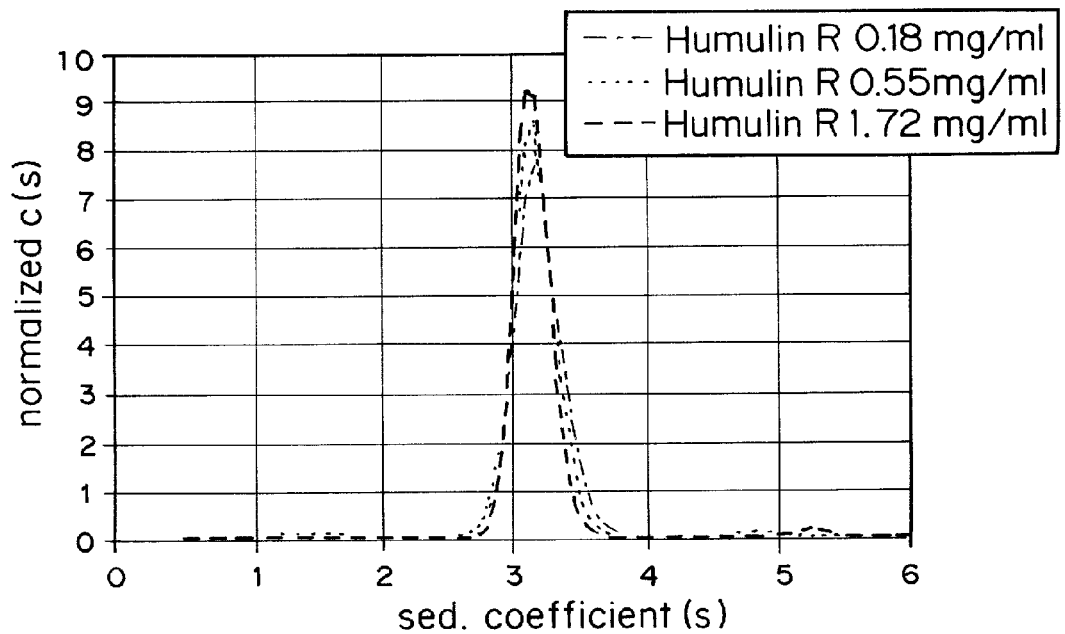
FIG. 10A is a graph of the c(s) distributions normalized to the loading concentration for sedimentation coefficients of RHI at concentrations of 0.18, 0.55, and 1.72 mg/ml.

FIG. 10A shows a plot of the c(s) distributions normalized to the loading concentration. The data shown for the normalized c(s) plot is consistent with the g(s*) data from DcDt+. The c(s) plots are nearly coincidental but there is a small shift to lower values of S in the sedimentation with an increase in concentration.

There appears to be a small amount (<1%) of slower sedimenting material in the two lowest concentration samples, and a small amount (<3%) of faster sedimenting species that is probably a dimer of the hexamer. The decrease in the slower species and an increase in the faster species with increasing concentration implies that there is only a very slight shift in the self-association of RHI over the concentration range studies.

The values obtained for the weight average sedimentation coefficient for each loading concentration, corrected to standard conditions, is given in the table below:

| Cell # | S (20, w) (Svedbergs) | Conc. (mg/ml) |
|---|---|---|
| 1 | 3.25 | 0.176 |
| 2 | 3.24 | 0.552 |
| 3 | 3.35 | 1.721 |

Conclusions:

These analyses indicate that the RHI, under the conditions of this experiment, exists primarily as a hexamer. There is a very small amount of slower sedimenting material present in the lower concentration samples, as well as what appears to be dimers of the hexamers. The concentration studies were approximately 30 μM, 100μ, and 300 μM (monomer units).

IL

Methods described above.

Results

Figure 10B:
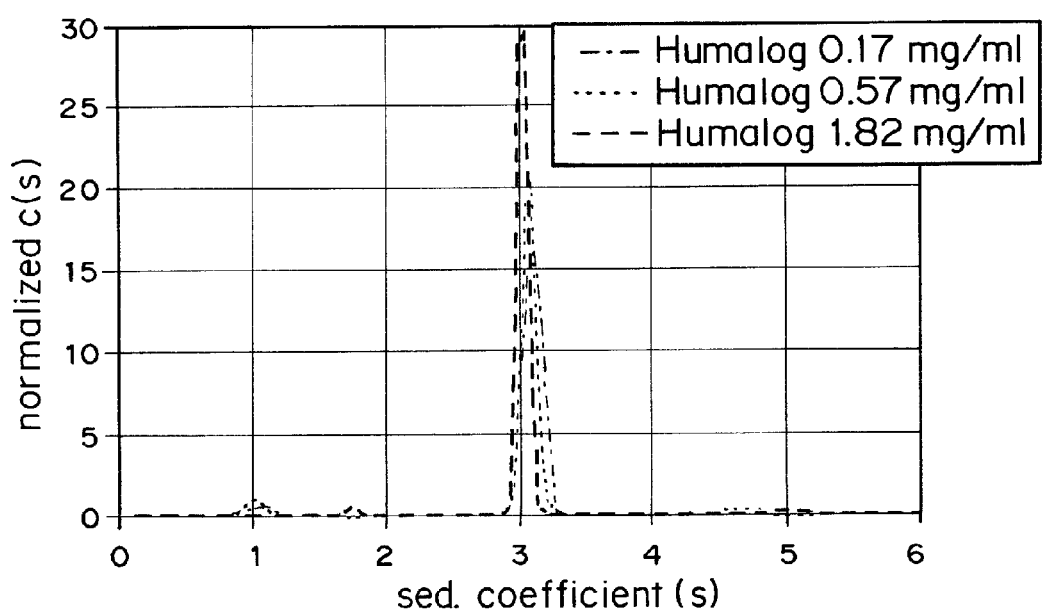
FIG. 10B is a graph of the c(s) distributions normalized to the loading concentration for sedimentation coefficients of IL at concentrations of 0.17, 0.57, and 1.82 mg/ml.

FIG. 10B shows a plot of the c(s) distributions normalized to the loading concentration. The data shown for the normalized c(s) plot is consistent with the g(s*) data from DcDt+. The c(s) curves at low concentration show a significant contribution of a smaller species (perhaps dimer) which decreases as the concentration is increased. There is also a slight shift to lower values of S in the sedimentation with an increase in concentration.

There appears to be a small amount (<2%) of faster sedimenting species, especially evident in the two higher concentration samples.

The values obtained for the weight average sedimentation coefficient for each loading concentration, corrected to standard conditions, is given in the table below:

| Cell # | S (20, w) (Svedbergs) | Conc. (mg/ml) |
| --- | --- | --- |
| 1 | 3.17 | 0.167 |
| 2 | 3.12 | 0.568 |
| 3 | 3.17 | 1.820 |

Conclusions:

These analyses indicate that IL, under the conditions of this experiment, exists primarily as a hexamer. There is evidence of the dissociation of IL upon dilution, and there is a small amount of what appears to be dimers of the hexamers present. The concentrations studies were approximately 30 μM, 100μ, and 300 μM (monomer units).

Insulin Aspart (IA)

Methods described above.

Results

Figure 10C:
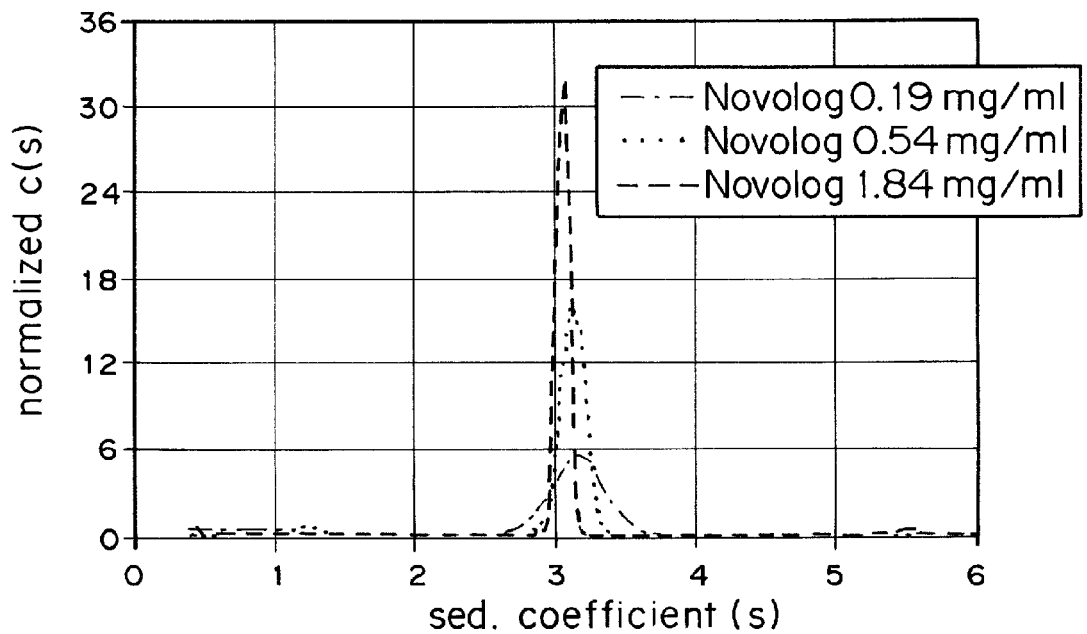
FIG. 10C is a graph of the c(s) distributions normalized to the loading concentration for sedimentation coefficients of IA at concentrations of 0.19, 0.54, and 1.84 mg/ml.

FIG. 10C shows a plot of c(s) distributions normalized to the loading concentration. The data shown for the normalized c(s) plot is consistent with the g(s*) data from DcDt+. The C(s) curves at low concentrations show a small amount of a smaller species (monomer/dimer) which decreases as the concentration is increased. There is also a slight shift to lower values of S in the sedimentation with an increase in concentration. The graph clearly shows that the protein is slightly dissociating upon dilution. In addition, there appears to be a small amount (approximately 3% in the highest concentration sample) of a faster sedimenting species that is may be a dimer of the hexamer.

The values obtained for the weight average sedimentation coefficient for each loading concentration, corrected to standard conditions, is given in the table below:

| Cell # | S (20, w) (Svedbergs) | Conc. (mg/ml) |
| --- | --- | --- |
| 1 | 3.10 | 0.186 |
| 2 | 3.23 | 0.544 |
| 3 | 3.24 | 1.848 |

Conclusion:

These analyses indicate that the IA, under the conditions of this experiment, exists primarily as a hexamer. There is evidence of the dissociation of IA upon dilution, and there is a small amount of what appears to bedimers of the hexamers present. The concentrations studies were approximately 30 μM, 100μ, and 300 μM (monomer units).

D. CE 100-4

Materials

The estimated stock concentration was 0.936 mg/ml after diluting one volume of the solution with three volumes of the supplied ECF.

Method

The dilution scheme, using the stock solution, for the four cells used in the analysis is shown in the following table:

| Cell # | Vol. Stock (μl) | Vol. Buffer (μl) | Est. Conc. (mg/ml) |
| --- | --- | --- | --- |
| 1 | 90 | 360 | 0.19 |
| 2 | 200 | 250 | 0.42 |
| 3 | 450 | — | 0.94 |

Results

Figure 10D:
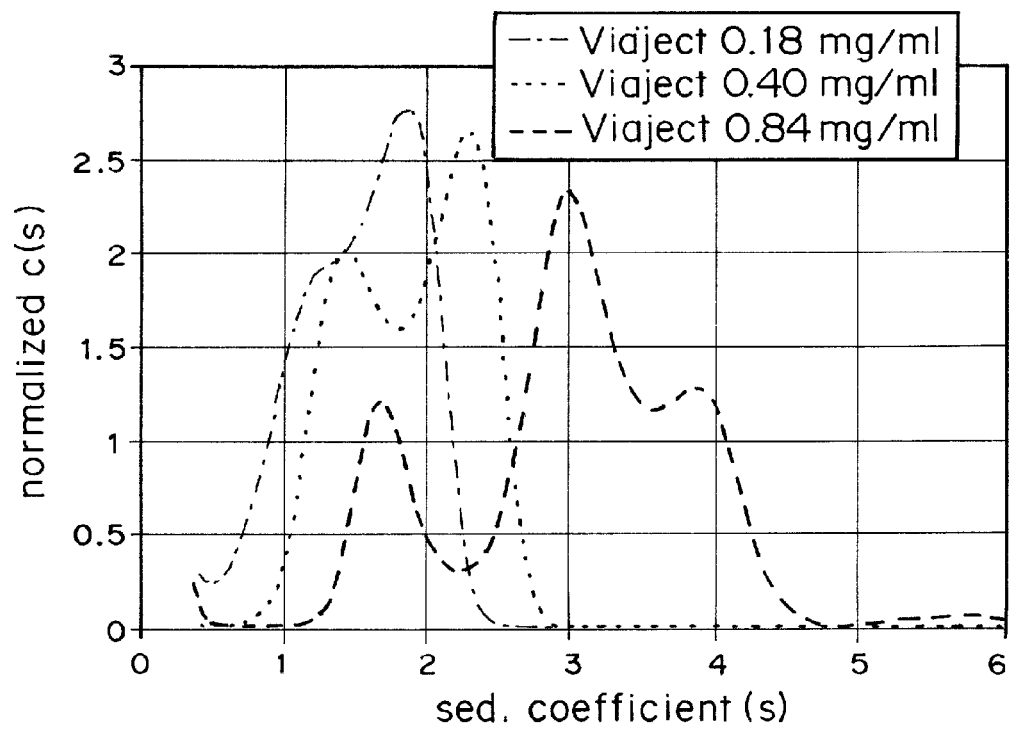
FIG. 10D is a graph of the c(s) distributions normalized to the loading concentration for sedimentation coefficients of CE100-4 at concentrations of 0.18, 0.40, and 0.84 mg/ml.

The datasets for CE 100-4 were analyzed using Sedfit and the c(s) model. Strictly speaking this model is only applicable to non-interacting mixtures but in the case of interacting species it can still yield an idea of what species are present in solution. FIG. 10D shows a plot of the c(s) distributions normalized to the loading concentration. The c(s) plot is consistent with the g(s*) data from DcDt+ in that there is a marked shift towards lower S values upon dilution. The c(s) plot from the highest concentration clearly shows that CE 100-4 may be larger than a hexamer. The values obtained for the weight average sedimentation coefficient for each loading concentration, corrected to standard conditions, is given in the table below:

| Cell # | S (20, w) (Svedbergs) | Conc. (mg/ml) |
| --- | --- | --- |
| 1 | 1.61 | 0.178 |
| 2 | 1.95 | 0.40 |
| 3 | 3.14 | 0.84 |

These analyses indicate that the CE 100-4, under the conditions of this experiment, exists in equilibrium between monomers, dimers, hexamers, and possibly larger oligomers at the highest concentration. The concentrations studied were approximately 30 μM, 70 μM, and 145 μM (monomer units).

Controls in Water Adjusted with HCl pH 2 or NaOH pH 7

The following physical constants were calculated for the amino acid composition for the protein using the program Sednterp.[5]

IC-pH7: $MW_{seq}$=5792 Da, $N_{20°}$=0.726 ml/g

The diluent density and viscosity were calculated to be 0.99823 g/ml and 0.01002 poise at 20° C., respectively, using Sednterp.

Internal Control IC pH7

Method

The dilution scheme, using water with NaOH, pH 7 as the diluent for the four cells used in the analysis is shown in the following table:

| Cell # | Vol. Stock (µl) | Vol. Buffer (µl) | Est. Conc. (mg/ml) |
|---|---|---|---|
| 1 | 25 | 475 | 0.19 |
| 2 | 75 | 375 | 0.62 |
| 3 | 250 | 250 | 1.87 |
| 3 | 450 | — | 3.745 |

Continuous sedimentation coefficient distribution, c(s).

The c(s) distribution plots are sharpened, relative to other analysis methods, because the broadening effects of diffusion are removed by use of an average value for the frictional coefficient.

Results

Figure 11:
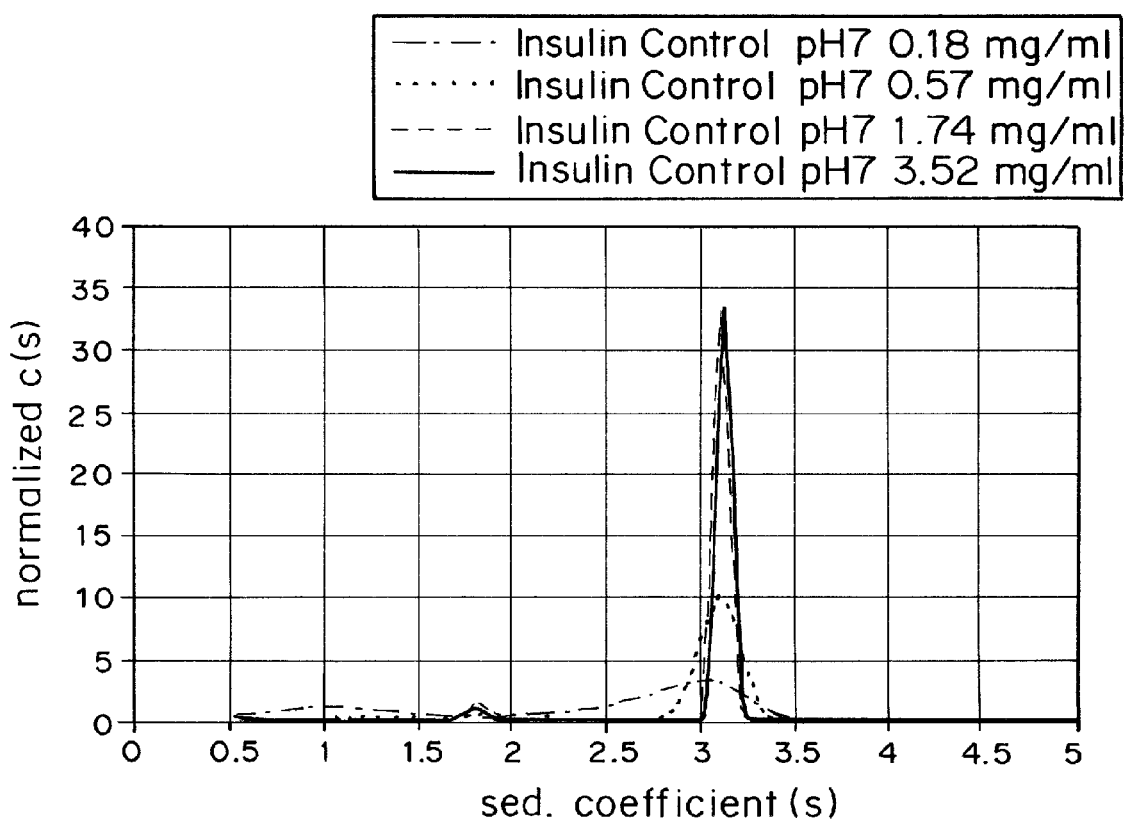
FIG. 11 is a graph of the c(s) distributions normalized to the loading concentration for sedimentation coefficients of control insulin pH 7 at concentrations of 0.18, 0.57, 1.74 and 3.52 mg/ml.

The datasets for IC-pH7 were analyzed using Sedfit and the c(s) model. Strictly speaking this model is only applicable to non-interacting mixtures but in the case of interacting species it can still yield an idea of what species are present in solution. FIG. 11 shows a plot of the c(s) distributions normalized to the loading concentration. The c(s) plot is consistent with the g(s*) data from DcDt+ in that there is a marked shift towards lower S values upon dilution.

The values obtained for the weight average sedimentation coefficient for each loading concentration, corrected to standard conditions, is given in the table below.

| Cell # | S (20, w) (Svedbergs) | Conc. (mg/ml) |
|---|---|---|
| 1 | 2.43 | 0.18 |
| 2 | 2.90 | 0.57 |
| 3 | 3.04 | 1.74 |
| 4 | 3.10 | 3.52 |

The analyses indicate that the sample, IC-pH7, under the conditions of this experiment, exists in a dimer-hexamer equilibrium at the lowest dilution, strongly favoring the hexameric state at the three highest concentrations used here. The concentrations studies were approximately 30 µM, 100 µM, 305 µM, and 620 µM (monomer units).

Internal Control IC pH 2

Method:

Insulin was diluted with 0.1N HCl as described above.

Results:

The datasets for IC-pH2 were analyzed using Sedfit and the c(s) model primarily to obtain a good estimate of the loading concentrations. The values obtained for the weight average sedimentation coefficient for each loading concentration agreed fairly well with the values determined using DcDt+. A table of the $S_{20,w}$ values as determined using Sedfit is given below.

| Cell # | S (20, w) (Svedbergs) | Conc. (mg/ml) |
|---|---|---|
| 1 | 1.26 | 0.17 |
| 2 | 1.28 | 0.56 |
| 3 | 1.28 | 1.77 |
| 4 | 1.28 | 3.61 |

These analyses indicate that the IC-pH2, under the conditions of this experiment, exists primarily as a single species (presumably the insulin monomer) showing no tendency toward further self-association. The solvent conditions were highly non-ideal due to the lack of any supporting electrolyte. The concentrations studied were 30 µM, 97 µM, 305 µM, and 620 µM (monomer units).

Overall Conclusions, Sedimentation Analysis

Estimation of RHI molecular weight, using DcDt software, established that its molecular weight is consistent with a hexamer (35.6±1.6 kDa) over the entire dilution range. The control values for pH 2 insulin, which is the standard for monomeric insulin (2.29 nm), has a sedimentation coefficient value of 1.28 S(20,w) that remains essentially unchanged over the dilution series, confirming its monomeric state. The control unstabilized insulin, pH 7 at full concentration is hexameric, but is in dynamic equilibrium with smaller dimer forms, as demonstrated by the reduction in size on dilution in pH 7 diluent. IA and IL start in the hexamer size range and has a small population of monomer/dimer forms after dilution to 1:16 in ECF. A higher proportion of monomeric/dimeric particles with CE 100-4 is consistent with its more rapid absorption profile.

Example 10

Determination of Effect on Insulin Size by Addition of Sodium Citrate and EDTA to Insulin, pH 7.4

Since the elevation in pH to 7 of the CES 100-4 showed rapid absorption in the swine model and a reduction in size by Malvern, an alternative method was designed to see if a substitution of the citric acid for trisodium citrate would also work at pH 7.4.

Materials and Methods

Disodium EDTA (1.8 mg/mL) and trisodium citrate (1.8 mg/mL) were dissolved in water with glycerin (22 mg/mL). Insulin was added to the solution at a concentration of 3.8 mg/mL. Sodium Hydroxide was added dropwise to elevate the pH to 7.4. The undiluted material was then analyzed on the Malvern for mean particle size, and then diluted with extracellular fluid buffer (ECF) and sized at each point along the dilution series.

Results

Figure 12:
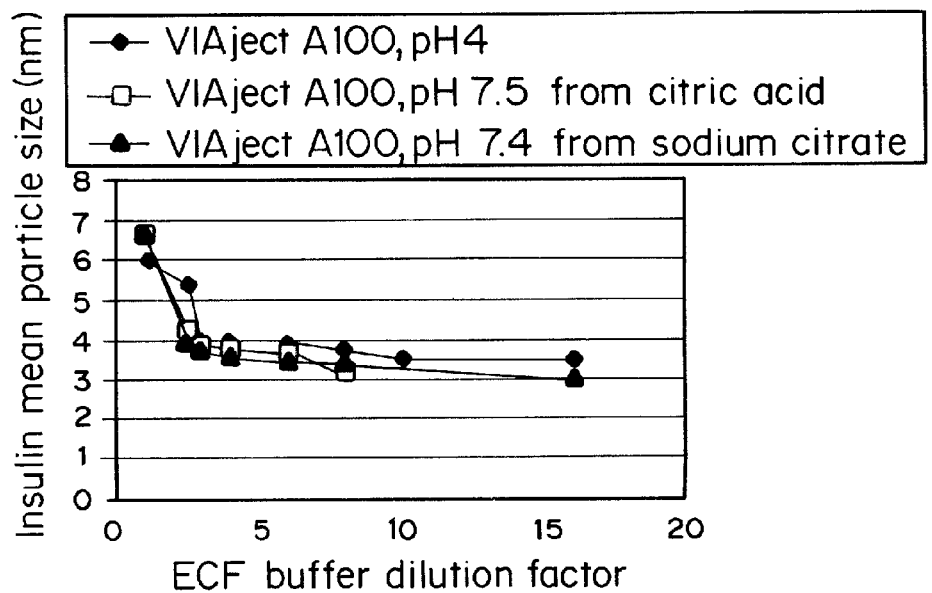
FIG. 12 is a graph of the insulin mean particles size (nm) as a function of dilution for CE 100-4, CE 100-7, and CRS 100-7.

CSE 100-7, Sodium Citrate Insulin pH 7.4, diluted with ECF buffer was compared to a citric acid formulation in an acid and neutral environment. The results are shown in FIG. 12. FIG. 12 is a graph of the insulin mean particles size (nm) as a function of dilution for CE 100-7 pH 7.5, and CSE 100-7 containing sodium citrate instead of citric acid, pH 7.4.

The results demonstrate that a rapidly dissociating insulin may be created by mixing sodium citrate, EDTA and insulin in solution at a neutral pH. The mean particle size initially is larger than a typical hexamer, presumably indicating that the hexamer is dissociating and is in the form of a loosely associated multimer of insulin molecules. On 1:2 dilution in a post injection environment (dilution in ECF), the insulin rapidly dissociates into smaller units, most likely insulin dimers. The new formulation behaves exactly as a citric acid/EDTA insulin formulation initially made at pH 4 and then brought to pH 7.

Example 11

Citric Acid EDTA Insulin pH 7 in Diabetic Miniature Swine

Materials and Methods

Insulin was prepared by mixing Insulin (3.8 mg/ml), disodium EDTA (18 mg/mL), Citric Acid (1.8 mg/mL), glycerin and m-cresol (3 mg/mL) and adjusting the pH to 4 with HCl. The pH of the solution was then raised to pH 7 by addition of NaOH. This briefly brought the formulation through the isoelectric point of the insulin creating a cloudy mixture that clarified when the final pH of 7.4 was reached. The CE 100-7 was given as a prandial insulin to swine before a meal.

Six male diabetic miniature swine (30-50 kg) were first administered 0.25 U/kg of the test insulin, then immediately fed 500 g standard pig food. Blood samples were obtained before feeding at −30, −20, −10, 0 minutes, then 5, 10, 15, 20, 30, 45, 60, 75, 90, 120, 150, 180, 240, 300, 360, 420, 480 min. post dose. Two mL blood samples were obtained via a jugular vein catheter of which one drop was used to check glucose measurement using a standard glucose strip method and the remaining sample was treated with $K_2EDTA$ and plasma sample was frozen for future analysis.

Results

Figure 13:
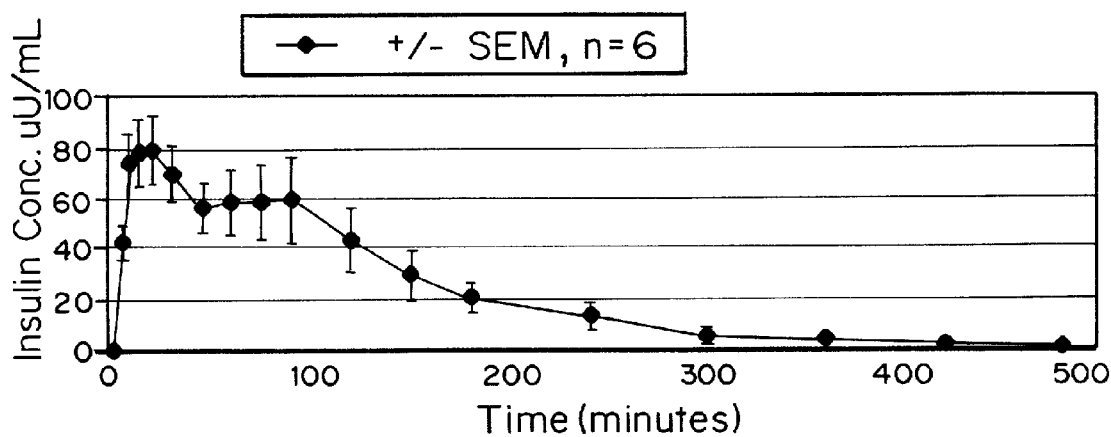
FIG. 13 is a graph of the insulin concentration (μunits/ml) by ELISA over time (minutes) in diabetic miniature swine.

Pharmacokinetic profile of the pH 7 formulation is shown in FIG. 13. This very rapid profile is consistent with data shown in patients with diabetes in Example 6. The elevation of the pH to 7 of the acid formulation containing citric acid and EDTA performed very well in miniature diabetic swine. This pH change resulted in the citric acid becoming sodium citrate. Therefore, the salt form of the acid works should work as well as the acid.

Modifications and variations of the present invention will be obvious to those skilled in the art from the foregoing description and are intended to come within the scope of the appended claims.

We claim:

1. A clear insulin solution having a pH of between greater than 7.0 and 7.6, consisting of insulin, one or more zinc chelators one or more dissolution agents and one or more excipients,
   wherein the insulin comprises dissociated insulin monomers produced by chelation of the zinc in insulin hexamers which are not soluble at a pH of between greater than 7.0 and 7.6,
   the dissociated insulin monomers have bound thereto charge masking agents which stabilize the dissociated insulin monomers,
   wherein the solution is prepared by raising the pH of an insulin solution from about pH 4.0 to a pH between a pH greater than 7.0 and a pH about 7.6, and
   wherein the insulin has an enhanced rate of uptake and transport through epithelial cells relative to the solution without the zinc chelator and dissolution agent.

2. The solution of claim 1, wherein the zinc chelator is selected from the group consisting of ethylenediaminetetraacetic acid (EDTA), ethylene-bis(oxyethylene nitro) tetraacetic acid (EGTA), trisodium citrate (TSC), alginic acid, alpha lipoic acid, dimercaptosuccinic acid (DMSA), and CDTA (1,2-diaminocyclohexanetetraacetic acid).

3. The solution of claim 2, wherein the zinc chelator is ethylenediaminetetraacetic acid (EDTA).

4. The solution of claim 1, wherein the dissolution agent is acetic acid, ascorbic acid, citric acid, glutamic, succinic, aspartic, maleic, fumaric, adipic acid, or a salt thereof.

5. The solution of claim 1 wherein the dissolution agent is citric acid or sodium citrate.

6. The solution of claim 1 wherein the pH is between 7.4 and 7.5.

7. The solution of claim 1, wherein the insulin is selected from the group consisting of human insulin, insulin analogs and combinations thereof.

8. The solution of claim 7 wherein the insulin is recombinant human insulin.

9. The solution of claim 7, wherein the insulin analog is selected from the group consisting of insulin lispro, insulin glargine, insulin aspart, insulin glulisine, and insulin detemir.

10. The solution of claim 1 provided as a frozen pharmaceutically acceptable solution for treatment of a diabetic.

11. The solution of claim 1 provided as a clear aqueous solution at 4° C.

12. A method of treating a diabetic individual comprising injecting an effective amount of a clear insulin solution having a pH of between greater than 7.0 and 7.6, consisting of insulin, a one or more zinc chelators, one or more dissolution agents and one or more excipients,
   wherein the insulin comprises dissociated insulin monomers produced by chelation of the zinc in insulin hexamers which are not soluble at a pH of between greater than 7.0 and 7.6 by a zinc chelator,
   the dissociated insulin monomers have bound thereto charge masking agents which stabilize the dissociated insulin monomers,
   wherein the solution is prepared by raising the pH of an insulin solution from about pH 4.0 to a pH between a pH greater than 7.0 and a pH about 7.6, and
   wherein the insulin has an enhanced rate of uptake and transport through epithelial cells relative to the solution without the zinc chelator and dissolution agent.

13. The method of claim 12 wherein the zinc chelator is selected from the group consisting of ethylenediaminetetraacetic acid (EDTA), ethylene-bis(oxyethylene nitro) tetraacetic acid (EGTA), trisodium citrate (TSC), alginic acid, alpha lipoic acid, dimercaptosuccinic acid (DMSA), and CDTA (1,2-diaminocyclohexanetetraacetic acid).

14. The method of claim 12 wherein the zinc chelator is ethylenediaminetetraacetic acid (EDTA).

15. The method of claim 12 wherein the dissolution agent is acetic acid, ascorbic acid, citric acid, glutamic, succinic, aspartic, maleic, fumaric, adipic acid, or a salt thereof.

16. The method of claim 15 wherein the dissolution agent is citric acid or sodium citrate.

17. The method of claim 12 wherein the pH is between 7.4 and 7.5.

18. The method of claim 12 wherein the insulin is selected from the group consisting of human insulin, insulin analogs and combinations thereof.

19. The method of claim 12 wherein the insulin is recombinant human insulin.

20. A clear insulin solution having a pH of between a pH greater than 7 and a pH of 7.6, wherein the solution consists of insulin, zinc chelator, dissolution agent and one or more excipients, wherein the solution is prepared by raising the pH of an insulin solution from about pH 4.0 to a pH of between a pH greater than 7.0 and a pH of 7.6.

* * * * *